(12) United States Patent
Blaschuk et al.

(10) Patent No.: US 6,391,855 B1
(45) Date of Patent: May 21, 2002

(54) COMPOUNDS AND METHODS FOR MODULATING JUNCTIONAL ADHESION MOLECULE-MEDIATED FUNCTIONS

(75) Inventors: Orest W. Blaschuk, Westmount; James Matthew Symonds, Ottawa; Barbara J. Gour, Kemptville, all of (CA)

(73) Assignee: Adherex Technologies, Inc., Ottawa (CA)

( * ) Notice: Subject to any disclaimer, the term of this patent is extended or adjusted under 35 U.S.C. 154(b) by 0 days.

(21) Appl. No.: 09/324,541

(22) Filed: Jun. 2, 1999

(51) Int. Cl.[7] .................. A61K 38/04; A61K 38/17; C07K 7/04; C07K 17/00
(52) U.S. Cl. .................. 514/17; 514/12; 514/13; 514/14; 514/15; 514/16; 530/324; 530/326; 530/327; 530/328; 530/329; 530/330
(58) Field of Search ................ 530/326, 330, 530/329, 328, 327, 402, 324; 514/12, 13, 14, 15, 16, 17

(56) References Cited

FOREIGN PATENT DOCUMENTS

| WO | WO 98/02452 | * | 1/1998 |
| WO | WO 98/24897 | | 6/1998 |

OTHER PUBLICATIONS

Kwon et al., "Backleak, Tight Junctions, and Cell–Cell Adhesion in Postischemic Injury to the Renal Allograft," *J. Clin. Invest. 101*(10): 2054–2064, 1998.

Martin–Padura et al., "Junctional Adhesion Molecule, a Novel Member of the Immunoglobulin Superfamily That Distributes at Intercellular Junctions and Modulates Monocyte Transmigration," *The Journal of Cell Biology 142*(1): 117–127, 1998.

\* cited by examiner

*Primary Examiner*—David Saunders
*Assistant Examiner*—Amy DeCloux
(74) *Attorney, Agent, or Firm*—SEED Intellectual Property Law Group PLLC

(57) ABSTRACT

Methods for using modulating agents to enhance or inhibit junctional adhesion molecule (JAM)-mediated cell adhesion in a variety of in vivo and in vitro contexts are provided. The modulating agents comprise at least one JAM cell adhesion recognition sequence or an antibody or fragment thereof that specifically binds the JAM cell adhesion recognition sequence. Modulating agents may additionally comprise one or more cell adhesion recognition sequences recognized by other adhesion molecules. Such modulating agents may, but need not, be linked to a targeting agent, drug and/or support material.

14 Claims, 2 Drawing Sheets

FIG. 1

SEHDGSPPSEYSWFKDGISMLTADAKKTRAFMNSSFTIDPKSGDLIFDPVTAFDSGEYY

SEQUENCE LISTING

<160> NUMBER OF SEQ ID NOS: 14

<210> SEQ ID NO 1
<211> LENGTH: 9
<212> TYPE: PRT
<213> ORGANISM: Artificial Sequence
<220> FEATURE:
<223> OTHER INFORMATION: Junction adhesion molecul e cell adhesion
      recognition sequence

<400> SEQUENCE: 1

Ser Phe Thr Ile Asp Pro Lys Ser Gly
 1               5

<210> SEQ ID NO 2
<211> LENGTH: 59
<212> TYPE: PRT
<213> ORGANISM: Mus musculus

<400> SEQUENCE: 2

Ser Glu His Asp Gly Ser Pro Pro Ser Glu T yr Ser Trp Phe Lys Asp
 1               5                  10                  15

Gly Ile Ser Met Leu Thr Ala Asp Ala Lys L ys Thr Arg Ala Phe Met
             20                  25                  30

Asn Ser Ser Phe Thr Ile Asp Pro Lys Ser G ly Asp Leu Ile Phe Asp
         35                  40                  45

Pro Val Thr Ala Phe Asp Ser Gly Glu Tyr T yr
     50                  55

```
<210> SEQ ID NO 3
<211> LENGTH: 5
<212> TYPE: PRT
<213> ORGANISM: Artificial Sequence
<220> FEATURE:
<223> OTHER INFORMATION: Cyclic CAR sequence fo r modulating JAM-mediated
      functions

<400> SEQUENCE: 3

Cys Asp Pro Lys Cys
1               5

<210> SEQ ID NO 4
<211> LENGTH: 6
<212> TYPE: PRT
<213> ORGANISM: Artificial Sequence
<220> FEATURE:
<223> OTHER INFORMATION: Modulating agent with JAM cell adhesion
      recognition sequences

<400> SEQUENCE: 4

Asp Pro Lys Asp Pro Lys
1               5

<210> SEQ ID NO 5
<211> LENGTH: 10
<212> TYPE: PRT
<213> ORGANISM: Artificial Sequence
<220> FEATURE:
<223> OTHER INFORMATION: Adhesion Molecule which is bound by N-CAM

<400> SEQUENCE: 5

Lys Tyr Ser Phe Asn Tyr Asp Gly Ser Glu
1               5                   10

<210> SEQ ID NO 6
<211> LENGTH: 4
<212> TYPE: PRT
<213> ORGANISM: Artificial Sequence
<220> FEATURE:
<223> OTHER INFORMATION: Occludin cell adhesion recognition sequence

<400> SEQUENCE: 6

Leu Tyr His Tyr
1

<210> SEQ ID NO 7
<211> LENGTH: 4
<212> TYPE: PRT
<213> ORGANISM: Artificial Sequence
<220> FEATURE:
<223> OTHER INFORMATION: Claudin cell adhesion recognition sequence

<400> SEQUENCE: 7

Ile Tyr Ser Tyr
1

<210> SEQ ID NO 8
<211> LENGTH: 4
<212> TYPE: PRT
<213> ORGANISM: Artificial Sequence
<220> FEATURE:
<223> OTHER INFORMATION: Synthetic peptide - Ex ample of cyclization
      process

<400> SEQUENCE: 8

Trp Gly Gly Trp
```

```
1

<210> SEQ ID NO 9
<211> LENGTH: 15
<212> TYPE: PRT
<213> ORGANISM: Artificial Sequence
<220> FEATURE:
<223> OTHER INFORMATION: Fab fragment directed against N-cadherin cell
      adhesion recognition sequence

<400> SEQUENCE: 9

Phe His Leu Arg Ala His Ala Val Asp Ile A sn Gly Asn Gln Val
 1               5                  10                  15

<210> SEQ ID NO 10
<211> LENGTH: 9
<212> TYPE: PRT
<213> ORGANISM: Artificial Sequence
<220> FEATURE:
<223> OTHER INFORMATION: Fab fragment directed against VE-cadherin cell
      adhesion recognition sequence

<400> SEQUENCE: 10

Val Phe Arg Val Asp Ala Glu Thr Gly
 1               5

<210> SEQ ID NO 11
<211> LENGTH: 8
<212> TYPE: PRT
<213> ORGANISM: Artificial Sequence
<220> FEATURE:
<223> OTHER INFORMATION: Fab fragment directed against claudin cell
      adhesion recognition sequence

<400> SEQUENCE: 11

Trp Lys Ile Tyr Ser Tyr Ala Gly
 1               5

<210> SEQ ID NO 12
<211> LENGTH: 10
<212> TYPE: PRT
<213> ORGANISM: Artificial Sequence
<220> FEATURE:
<223> OTHER INFORMATION: Fab fragment directed against occludin cell
      adhesion recognition sequence

<400> SEQUENCE: 12

Gln Tyr Leu Tyr His Tyr Cys Val Val Asp
 1               5                  10

<210> SEQ ID NO 13
<211> LENGTH: 9
<212> TYPE: PRT
<213> ORGANISM: Artificial Sequence
<220> FEATURE:
<223> OTHER INFORMATION: Fab fragment directed against OB-cadherin cell
      adhesion recognition sequence

<400> SEQUENCE: 13

Ile Phe Val Ile Asp Asp Lys Ser Gly
 1               5

<210> SEQ ID NO 14
<211> LENGTH: 10
<212> TYPE: PRT
<213> ORGANISM: Artificial Sequence
<220> FEATURE:
<223> OTHER INFORMATION: Fab fragment directed against E-cadherin cell
```

-continued adhesion recognition sequence

<400> SEQUENCE: 14

Leu Phe Ser His Ala Val Ser Ser Asn Gly
 1               5                  10

COMPOUNDS AND METHODS FOR MODULATING JUNCTIONAL ADHESION MOLECULE-MEDIATED FUNCTIONS

TECHNICAL FIELD

The present invention relates generally to methods for regulating processes mediated by junctional adhesion molecule (JAM), and more particularly to the use of modulating agents comprising a JAM cell adhesion recognition sequence and/or an antibody that specifically recognizes such a sequence for inhibiting functions such as cell adhesion and the formation of tissue permeability barriers.

BACKGROUND OF THE INVENTION

Cell adhesion is a complex process that is important for maintaining tissue integrity and generating physical and permeability barriers within the body. All tissues are divided into discrete compartments, each of which is composed of a specific cell type that adheres to similar cell types. Such adhesion triggers the formation of intercellular junctions (i.e., readily definable contact sites on the surfaces of adjacent cells that are adhering to one another), also known as tight junctions, gap junctions, spot desmosomes and belt desmosomes. The formation of such junctions gives rise to physical and permeability barriers that restrict the free passage of cells and other biological substances from one tissue compartment to another. For example, the blood vessels of all tissues are composed of endothelial cells. In order for components in the blood to enter a given tissue compartment, they must first pass from the lumen of a blood vessel through the barrier formed by the endothelial cells of that vessel. Similarly, in order for substances to enter the body via the gut, the substances must first pass through a barrier formed by the epithelial cells of that tissue. To enter the blood via the skin, both epithelial and endothelial cell layers must be crossed.

Cell adhesion is mediated by specific cell surface adhesion molecules (CAMs). There are many different families of CAMs, including the immunoglobulin, integrin, selectin and cadherin superfamilies, and each cell type expresses a unique combination of these molecules. Cadherins are a rapidly expanding family of calcium-dependent CAMs (Munro et al., *In: Cell Adhesion and Invasion in Cancer Metastasis*, P. Brodt, ed., pp. 17–34, RG Landes Co., Austin Tex., 1996). The cadherins (abbreviated CADs) are membrane glycoproteins that generally promote cell adhesion through homophilic interactions (a CAD on the surface of one cell binds to an identical CAD on the surface of another cell). Cadherins have been shown to regulate epithelial, endothelial, neural and cancer cell adhesion, with different CADs expressed on different cell types. For example, N (neural)—cadherin is predominantly expressed by neural cells, endothelial cells and a variety of cancer cell types. E (epithelial)—cadherin is predominantly expressed by epithelial cells. VE (vascular endothelial)—cadherin is predominantly expressed by endothelial cells. Other CADs are P (placental)—cadherin, which is found in human skin, and R (retinal)—cadherin. A detailed discussion of the cadherins is provided in Munro SB et al., 1996, *In: Cell Adhesion and Invasion in Cancer Metastasis*, P. Brodt, ed., pp. 17–34 (RG Landes Company, Austin Tex.) and Lampugnani and Dejana, *Curr. Opin. Cell Biol.* 9:674–682, 1997.

CAD-mediated cell adhesion triggers a cascade of events that lead to the formation of intercellular junctions, and ultimately to the establishment of permeability barriers between tissue compartments. The intercellular junction that is directly responsible for the creation of permeability barriers that prevent the diffusion of solutes through paracellular spaces is known as the tight junction, or zonula occludens (Anderson and van Itallie, *Am. J. Physiol.* 269:G467–G475, 1995; Lampugnani and Dejana, *Curr. Opin. Cell Biol.* 9:674–682, 1997).

The transmembrane component of tight junctions that has been the most studied is occludin (Furuse et al., *J. Cell Biol.* 123:1777–1788, 1993; Furuse et al., *J. Cell Sci.* 109:429–435, 1996). This protein appears to be expressed by all endothelial cell types, as well as by most epithelial cell types. Occludin is believed to be directly involved in cell adhesion and the formation of tight junctions (Furuse et al., *J. Cell Sci.* 109:429–435, 1996; Chen et al., *J. Cell Biol* 138:891–899, 1997). A detailed discussion of occludin structure and function is provided by Lampugnani and Dejana, *Curr. Opin. Cell Biol.* 9:674–682, 1997.

More recently, junctional adhesion molecule (JAM) has been identified as an immunoglobulin gene superfamily member that is a component of tight junctions (Martin-Padura et al., *J. Cell. Biol.* 142:117–127, 1998). This protein is selectively concentrated at intercellular junctions of endothelial and epithelial cells of different origins, and has been shown to play a role in regulating monocyte transmigration.

Although cell adhesion is required for certain normal physiological functions, there are situations in which the level of cell adhesion is undesirable. For example, many pathologies (such as autoimmune diseases and inflammatory diseases) involve abnormal cellular adhesion. Cell adhesion may also play a role in graft rejection. In such circumstances, modulation of cell adhesion may be desirable.

In addition, permeability barriers arising from cell adhesion create difficulties for the delivery of drugs to specific tissues and tumors within the body. For example, skin patches are a convenient tool for administering drugs through the skin. However, the use of skin patches has been limited to small, hydrophobic molecules because of the epithelial and endothelial cell barriers. Similarly, endothelial cells render the blood capillaries largely impermeable to drugs, and the blood/brain barrier has hampered the targeting of drugs to the central nervous system. In addition, many solid tumors develop internal barriers that limit the delivery of anti-tumor drugs and antibodies to inner cells.

Attempts to facilitate the passage of drugs across such barriers generally rely on specific receptors or carrier proteins that transport molecules across barriers in vivo. However, such methods are often inefficient, due to low endogenous transport rates or to the poor functioning of a carrier protein with drugs. While improved efficiency has been achieved using a variety of chemical agents that disrupt cell adhesion, such agents are typically associated with undesirable side-effects, may require invasive procedures for administration and may result in irreversible effects.

Accordingly, there is a need in the art for compounds that modulate cell adhesion and improve drug delivery across permeability barriers without such disadvantages. The present invention fulfills this need and further provides other related advantages.

SUMMARY OF THE INVENTION

The present invention provides compounds and methods for modulating JAM-mediated cell adhesion and the formation of permeability barriers. Within certain aspects, the present invention provides cell adhesion modulating agents that inhibit or enhance JAM-mediated cell adhesion. Certain modulating agents are 4–16 amino acid peptides (which may be linear or cyclic) that comprise the sequence Asp-Pro-Lys (DPK). Within other embodiments, a modulating agent may (a) comprise at least five or seven consecutive amino acid residues of a JAM CAR sequence having the formula:

Ser-Phe-Thr-Ile-Asp-Pro-Lys-Ser-Gly (SEQ ID NO:1)

and (b) contain no more than 50 consecutive amino acid residues present within a JAM.

Within certain embodiments, a modulating agent as described above comprises a JAM CAR sequence that is present within a cyclic peptide. The cyclic peptide may have the formula:

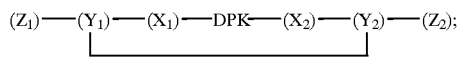

wherein $X_1$, and $X_2$ are optional, and if present, are independently selected from the group consisting of amino acid residues and combinations thereof in which the residues are linked by peptide bonds, and wherein $X_1$ and $X_2$ independently range in size from 0 to 10 residues, such that the sum of residues contained within $X_1$ and $X_2$ ranges from 1 to 12; wherein $Y_1$ and $Y_2$ are independently selected from the group consisting of amino acid residues, and wherein a covalent bond is formed between residues $Y_1$ and $Y_2$; and wherein $Z_1$ and $Z_2$ are optional, and if present, are independently selected from the group consisting of amino acid residues and combinations thereof in which the residues are linked by peptide bonds. In certain embodiments, $Y_1$ comprises an N-acetyl group and/or $Y_2$ comprises a C-terminal amide group. $Y_1$ and $Y_2$ may be covalently linked via any suitable bond, including a disulfide bond, an amide bond or a thioether bond.

The present invention further provides, within other aspects, polynucleotides encoding a modulating agent as provided above, expression vectors comprising such a polynucleotide, and host cells transformed or transfected with such an expression vector. Within further aspects, the present invention provides modulating agents that comprise an antibody or antigen-binding fragment thereof that specifically binds to a JAM CAR sequence as described above and modulates a JAM-mediated function.

The present invention further provides modulating agents comprising a mimetic of a JAM CAR sequence provided above, wherein the mimetic is capable of modulating a JAM-mediated function.

Within other aspects, modulating agents as described above may be linked to one or more of a drug, a detectable marker, a targeting agent and/or a support material. Alternatively, or in addition, modulating agents as described above may further comprise one or more of: (a) a cell adhesion recognition sequence that is bound by an adhesion molecule other than a JAM; and/or (b) an antibody or antigen-binding fragment thereof that specifically binds to a cell adhesion recognition sequence bound by an adhesion molecule other than a JAM. Such adhesion molecules may be selected from the group consisting of integrins, cadherins, occludin, N-CAM, claudins, PE-CAM, desmogleins, desmocollins, fibronectin, laminin and other extracellular matrix proteins.

The present invention further provides pharmaceutical compositions comprising a cell adhesion modulating agent as described above, in combination with a pharmaceutically acceptable carrier. Such compositions may further comprise a drug. In addition, or alternatively, such compositions may further comprise one or more of: (a) a peptide comprising a cell adhesion recognition sequence that is bound by an adhesion molecule other than a JAM; and/or (b) an antibody or antigen-binding fragment thereof that specifically binds to a cell adhesion recognition sequence bound by an adhesion molecule other than a JAM.

Within further aspects, methods are provided for modulating cell adhesion, comprising contacting a JAM-expressing cell with a cell adhesion modulating agent as described above.

Within one such aspect, the present invention provides methods for increasing vasopermeability in a mammal, comprising administering to a mammal a cell adhesion modulating agent as provided above, wherein the modulating agent inhibits JAM-mediated cell adhesion.

Within another aspect, methods are provided for reducing unwanted cellular adhesion in a mammal, comprising administering to a mammal a cell adhesion modulating agent as provided above, wherein the modulating agent inhibits JAM-mediated cell adhesion.

In yet another aspect, the present invention provides methods for enhancing the delivery of a drug through the skin of a mammal, comprising contacting epithelial cells of a mammal with a cell adhesion modulating agent as provided above and a drug, wherein the modulating agent inhibits JAM-mediated cell adhesion, and wherein the step of contacting is performed under conditions and for a time sufficient to allow passage of the drug across the epithelial cells.

The present invention further provides methods for enhancing the delivery of a drug to a tumor in a mammal, comprising administering to a mammal a cell adhesion modulating agent as provided above and a drug, wherein the modulating agent inhibits JAM-mediated cell adhesion.

Within further aspects, the present invention provides methods for treating cancer in a mammal, comprising administering to a mammal a cell adhesion modulating agent as provided above, wherein the modulating agent inhibits JAM-mediated cell adhesion.

The present invention further provides methods for inhibiting angiogenesis in a mammal, comprising administering to a mammal a cell adhesion modulating agent as provided above, wherein the modulating agent inhibits JAM-mediated cell adhesion.

Within further aspects, the present invention provides methods for enhancing drug delivery to the central nervous system of a mammal, comprising administering to a mammal a cell adhesion modulating agent as provided above, wherein the modulating agent inhibits JAM-mediated cell adhesion.

The present invention further provides methods for enhancing wound healing in a mammal, comprising contacting a wound in a mammal with a cell adhesion modulating agent as provided above, wherein the modulating agent enhances JAM-mediated cell adhesion.

Within a related aspect, the present invention provides methods for enhancing adhesion of foreign tissue implanted within a mammal, comprising contacting a site of implantation of foreign tissue in a mammal with a cell adhesion modulating agent as provided above, wherein the modulating agent enhances JAM-mediated cell adhesion.

The present invention further provides methods for inducing apoptosis in a JAM-expressing cell, comprising contacting a JAM-expressing cell with a cell adhesion modulating agent as provided above, wherein the modulating agent inhibits JAM-mediated cell adhesion.

The present invention further provides methods for modulating monocyte traffic in a mammal, comprising administering to a mammal a cell adhesion modulating agent as provided above.

The present invention further provides methods for identifying an agent capable of modulating JAM-mediated cell adhesion. One such method comprises the steps of (a) culturing cells that express a JAM in the presence and absence of a candidate agent, under conditions and for a time sufficient to allow cell adhesion; and (b) visually evaluating the extent of cell adhesion among the cells.

Within another embodiment, such methods may comprise the steps of: (a) culturing normal rat kidney cells in the presence and absence of a candidate agent, under conditions and for a time sufficient to allow cell adhesion; and (b) comparing the level of cell surface JAM and E-cadherin for cells cultured in the presence of candidate agent to the level for cells cultured in the absence of candidate agent.

Within a further embodiment, such methods may comprise the steps of: (a) culturing human aortic endothelial cells in the presence and absence of a candidate agent, under conditions and for a time sufficient to allow cell adhesion; and (b) comparing the level of cell surface JAM and N-cadherin for cells cultured in the presence of candidate agent to the level for cells cultured in the absence of candidate agent.

Within yet another embodiment, such methods comprise the steps of: (a) contacting an antibody that binds to a modulating agent comprising a JAM CAR sequence with a test compound; and (b) detecting the level of antibody that binds to the test compound.

The present invention further provides methods for detecting the presence of JAM-expressing cells in a sample, comprising: (a) contacting a sample with an antibody that binds to a JAM CAR sequence under conditions and for a time sufficient to allow formation of an antibody-JAM complex; and (b) detecting the level of antibody-JAM complex, and therefrom detecting the presence of JAM-expressing cells in the sample.

Within further aspects, the present invention provides kits for detecting the presence of JAM-expressing cells in a sample, comprising: (a) an antibody that binds to a modulating agent comprising a JAM CAR sequence; and (b) a detection reagent.

The present invention further provides, within other aspects, kits for enhancing transdermal drug delivery, comprising: (a) a skin patch; and (b) a cell adhesion modulating agent, wherein the modulating agent comprises a JAM CAR sequence, and wherein the modulating agent inhibits JAM-mediated cell adhesion.

These and other aspects of the invention will become evident upon reference to the following detailed description and attached drawings. All references disclosed herein are hereby incorporated by reference in their entirety as if each were individually noted for incorporation.

BRIEF DESCRIPTION OF THE DRAWINGS

FIG. 1 provides the amino acid sequence of the second extracellular immunoglobulin-like domain of a representative mouse JAM (SEQ ID NO:2). The JAM cell adhesion recognition region is shown in bold.

DETAILED DESCRIPTION OF THE INVENTION

Figure 2:
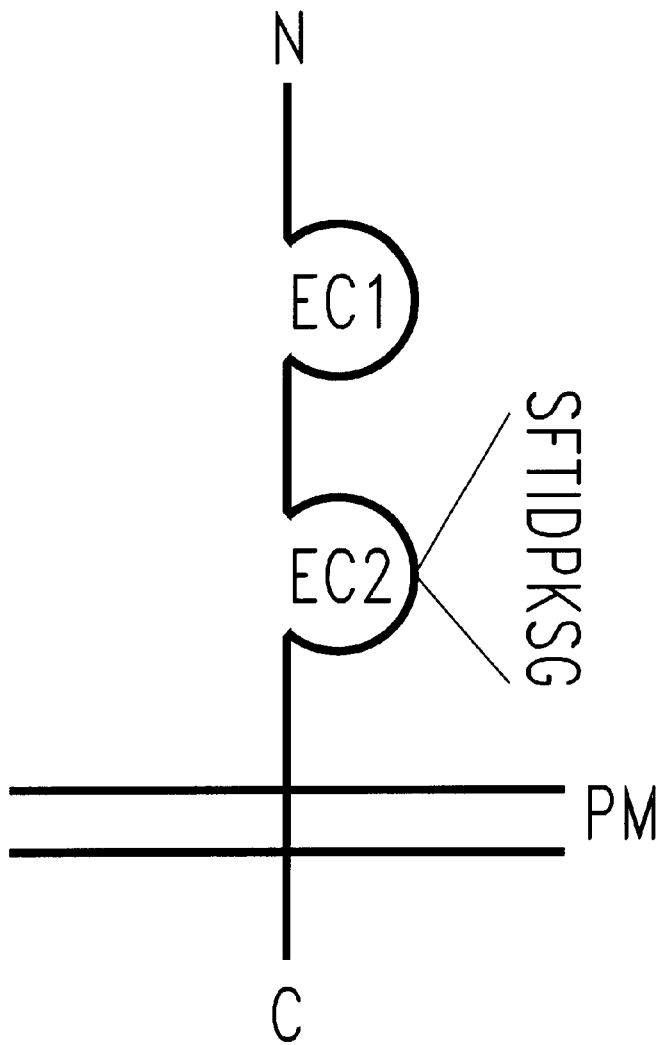
FIG. 2 is a schematic diagram illustrating the structure of JAM, a membrane glycoprotein, passing through the plasma membrane (PM). It possesses two extracellular immunoglobulin-like repeats (EC1, EC2), a transmembrane domain and a cytoplasmic region. The JAM CAR sequence SFTIDPKSG (SEQ ID NO:1) is present in EC2, where letters correspond to IUPAC amino acid symbols. 'N' represents the amino-terminus and 'C' represents the carboxy-terminus.

As noted above, the present invention provides cell adhesion modulating agents comprising peptides that are capable of modulating JAM-mediated processes, such as cell adhesion. The present invention is based on the identification of a previously unknown cell adhesion recognition (CAR) sequence present in JAM. A modulating agent may generally comprise one or more JAM CAR sequences (or analogues or mimetics thereof), with or without one or more additional CAR sequences, as described below. Peptide CAR sequences may be present within a linear or cyclic peptide. Alternatively, or in addition, a modulating agent may comprise a polynucleotide encoding a peptide comprising one or more JAM CAR sequences and/or a modulating agent may comprise a substance (such as an antibody or antigen-binding fragment thereof) that specifically binds to a JAM CAR sequence.

In general, to modulate JAM-mediated cell adhesion, a JAM-expressing cell is contacted with a cell adhesion modulating agent (also referred to herein as a "modulating agent") either in vivo or in vitro. JAM-expressing cells may be readily identified using any of a variety of techniques well known in the art (such as, for example, hybridization, PCR or immunohistochemical techniques), and include endothelial and epithelial cells, as well as cancer cells, such as carcinoma cells. Within certain aspects, the methods provided herein inhibit a JAM-mediated function. Such methods include, for example, methods for treating diseases or other conditions characterized by undesirable cell adhesion or for facilitating drug delivery to a specific tissue or tumor. Certain methods may inhibit cell adhesion (e.g., cancer cell adhesion), as well as cancer invasion and metastasis. Alternatively, a modulating agent may, such as when linked to a matrix or to another modulating agent via a linker, be used to enhance a JAM-mediated function, such as cell adhesion. Such conjugates may be used, for example, to facilitate wound healing or the adhesion of implants.

Cell Adhesion Modulating Agents

The term "cell adhesion modulating agent," as used herein, refers to a molecule comprising at least one of the following components:

(a) a linear or cyclic peptide sequence that is at least 50% identical to a JAM CAR sequence (i.e., a JAM CAR sequence or an analogue thereof that retains at least 50% identity);

(b) a mimetic (e.g., peptidomimetic or small molecule mimic) of a JAM CAR sequence;

(c) a substance such as an antibody or antigen-binding fragment thereof that specifically binds a JAM CAR sequence; and/or (d) a polynucleotide encoding a polypeptide that comprises a JAM CAR sequence or analogue thereof.

A modulating agent may consist entirely of one or more of the above elements, or may additionally comprise further peptide and/or non-peptide regions. Additional peptide regions may be derived from a JAM (preferably an extracellular domain that comprises a CAR sequence) and/or may be heterologous. Within certain preferred embodiments, a modulating agent contains no more than 85 consecutive amino acid residues, and preferably no more than 50 consecutive amino acid residues, present within a JAM.

A modulating agent is further capable of modulating a function mediated by a JAM. Such activity may generally be assessed using, for example, representative assays provided herein. Certain modulating agents inhibit an interaction between JAM molecules and/or between a JAM and a different adhesion molecule. For functions (e.g., cell adhesion) that are inhibited by a full length, soluble JAM, such a modulating agent may inhibit the function with an activity that is not substantially diminished relative to the full length JAM (i.e., the modulating agent inhibits the function at least as well as soluble JAM, when contacted with cells that express the JAM). For example, a modulating agent may be as effective as soluble JAM in preventing and/or disrupting adhesion of JAM-expressing cells. Alternatively, to enhance adhesion of JAM-expressing cells, a modulating agent may comprise an antibody or antigen-binding fragment thereof and/or multiple peptides or mimetics linked to a support material. Such modulating agents may function as a biological glue to bind JAM-expressing cells, and should result in a detectable enhancement of cell adhesion (preferably an enhancement that is at least as great as that observed for immobilized JAM or antibody directed against the JAM).

The term "JAM," as used herein, refers to an integral membrane protein that is selectively concentrated at intercellular junctions of endothelial and epithelial cells. JAM appears to have an extracellular domain containing two immunoglobulin-like loops, a transmembrane domain and a cytoplasmic domain, and has a molecular weight of approximately 36–43 kD. Mouse JAM has been reported by Martin-Padura et al., *J. Cell. Biol.* 142:117–127, 1998. JAMs from other species may be identified based on similarity in sequence to mouse JAM, and should generally display at least 50% sequence identity to mouse JAM. Such JAMs may further display structural similarity, such as similar numbers of immunoglobulin repeats, based on the generic JAM structure provided in FIG. 2, and may also display similar localization.

A JAM CAR sequence, as used herein, is an amino acid sequence that is present in a naturally occurring JAM and that is capable of detectably modulating a JAM-mediated function, such as cell adhesion, as described herein. In other words, contacting a JAM-expressing cell with a peptide comprising a CAR sequence results in a detectable change in a JAM-mediated function using at least one of the representative assays provided herein. CAR sequences may be of any length, but generally comprise at least three amino acid residues, preferably 4–16 amino acid residues, and more preferably 5–8 amino acid residues. A peptide modulating agent may comprise any number of amino acid residues, but preferred agents comprise 3–50 residues, preferably 4–16 residues. Within certain embodiments, a peptide modulating agent preferably comprises an N-acetyl group (i.e., the amino group present on the amino terminal residue of the peptide is acetylated). It has been found, within the context of the present invention, that the presence of such an acetyl group may enhance peptide modulating activity for certain applications.

JAM CAR sequences are generally physically located within the JAM molecule in or near the binding site of an adhesion molecule (i. e., within 10 amino acids, and preferably within 5 amino acids). The location of a binding site may generally be determined using well known techniques, such as evaluating the ability of a portion of the JAM to bind to the same JAM or to another molecule. Any standard binding assay may be employed for such an evaluation. Recognition of a CAR sequence by the JAM or other molecule results in a measurable effect on a JAM function, such as cell adhesion. Peptides comprising a CAR sequence generally inhibit such a function unless linked, as described herein, to form an enhancer of adhesion molecule function. It has been found, within the context of the present invention, that certain JAM CAR sequences comprise the sequence: Ser-Phe-Thr-Ile-Asp-Pro-Lys-Ser-Gly (SEQ ID NO:1).

Modulating agents provided herein may include at least a portion of such a CAR sequence. Additional JAM CAR sequences may be identified based on sequence homology to the JAM CAR sequence provided herein, and based on the ability of a peptide comprising such a sequence to modulate a JAM-mediated function within a representative assay described herein. Within certain embodiments, a modulating agent comprises at least three consecutive residues, preferably at least five consecutive residues and more preferably at least seven consecutive residues, of a JAM CAR sequence that satisfies the above consensus sequence. Preferred modulating agents comprise the sequence DPK.

Peptides comprising a greater number of consecutive residues derived from a JAM CAR sequence may have a greater specificity for that JAM. In addition, further flanking sequences may be included to enhance specificity. Such flanking sequences may be identified based on the sequences provided in FIG. 1, or based on published sequences.

As noted above, certain preferred modulating agents comprise a peptide (containing a JAM CAR sequence or an analogue thereof) in which at least one terminal amino acid residue is modified (e.g., the N-terminal amino group is modified by, for example, acetylation or alkoxybenzylation and/or an amide or ester is formed at the C-terminus). It has been found, within the context of the present invention, that the addition of at least one such group to a linear or cyclic peptide modulating agent may improve the ability of the agent to modulate a JAM-mediated function. Certain preferred modulating agents contain modifications at the N- and C-terminal residues, such as N-Ac-SFTIDPKSG-NH$_2$ (SEQ ID NO:1)

As noted above, the present invention further contemplates JAM CAR sequences from other organisms. Such CAR sequences may be identified based upon sequence similarity to the sequences provided herein, and the ability to modulate a JAM-mediated function may be confirmed as described herein.

As noted above, modulating agents as described herein may comprise an analogue or mimetic of a JAM CAR sequence. An analogue generally retains at least 50% identity to a native JAM CAR sequence, and modulates a JAM-mediated function as described herein. Such analogues preferably contain at least three residues of, and more preferably at least five residues of, a JAM CAR sequence. An analogue may contain any of a variety of amino acid substitutions, additions, deletions and/or modifications (e.g., side chain modifications). Preferred amino acid substitutions are conservative. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. The critical determining feature of a JAM CAR sequence analogue is the ability to modulate a JAM-mediated function, which may be evaluated using the representative assays provided herein.

A mimetic is a non-peptidyl compound that is conformationally similar to a JAM CAR sequence, such that it modulates a JAM-mediated function as described below. Such mimetics may be designed based on techniques that evaluate the three dimensional structure of the peptide. For example, Nuclear Magnetic Resonance spectroscopy (NMR) and computational techniques may be used to determine the conformation of a JAM CAR sequence. NMR is widely used for structural analyses of both peptidyl and non-peptidyl compounds. Nuclear Overhauser Enhancements (NOE's), coupling constants and chemical shifts depend on the conformation of a compound. NOE data provides the interproton distance between protons through space and can be used to calculate the lowest energy conformation for the JAM CAR sequence. This information can then be used to design mimetics of the preferred conformation. Linear peptides in solution exist in many conformations. By using conformational restriction techniques it is possible to fix the peptide in the active conformation. Conformational restriction can be achieved by i) introduction of an alkyl group such as a methyl which sterically restricts free bond rotation; ii) introduction of unsaturation which fixes the relative positions of the terminal and geminal substituents; and/or iii) cyclization, which fixes the relative positions of the sidechains. Mimetics may be synthesized where one or more of the amide linkages has been replaced by isosteres, substituents or groups which have the same size or volume such as —CH$_2$NH—, —CSNH—, —CH$_2$S—, —CH=CH—, —CH$_2$CH$_2$—, —CONMe— and others. These backbone amide linkages can also be part of a ring structure (e.g., lactam). Mimetics may be designed where one or more of the side chain functionalities of the JAM CAR sequence are replaced by groups that do not necessarily have the same size or volume, but have similar chemical and/or physical properties which produce similar biological responses. Other mimetics may be small molecule mimics, which may be readily identified from small molecule libraries, based on the three-dimensional structure of the CAR sequence. It should be understood that, within embodiments described below, an analogue or mimetic may be substituted for a JAM CAR sequence.

Modulating agents, or peptide portions thereof, may be linear or cyclic peptides. The term "cyclic peptide," as used herein, refers to a peptide or salt thereof that comprises (1) an intramolecular covalent bond between two non-adjacent residues, forming a peptide ring and (2) at least one JAM CAR sequence or an analogue thereof present within the peptide ring. The intramolecular bond may be a backbone to backbone, side-chain to backbone or side-chain to side-chain bond (i.e., terminal functional groups of a linear peptide and/or side chain functional groups of a terminal or interior residue may be linked to achieve cyclization). Preferred intramolecular bonds include, but are not limited to, disulfide, amide and thioether bonds. Any of the above JAM CAR sequences, or an analogue or mimetic thereof, may be incorporated into a cyclic peptide, with or without one or more other adhesion molecule CAR sequences. Additional adhesion molecule CAR sequences are described in greater detail below.

The size of a cyclic peptide ring generally ranges from 5 to about 15 residues, preferably from 5 to 10 residues. Additional residue(s) may be present on the N-terminal and/or C-terminal side of a JAM CAR sequence, and may be derived from sequences that flank a CAR sequence, with or without amino acid substitutions and/or other modifications. Alternatively, additional residues present on one or both sides of the CAR sequence(s) may be unrelated to an endogenous sequence (e.g., residues that facilitate cyclization, purification or other manipulation and/or residues having a targeting or other function).

Within certain embodiments, a modulating agent may comprise a cyclic peptide that contains a JAM CAR sequence as provided herein (or a portion of such a CAR sequence). Certain cyclic peptides have the formula:

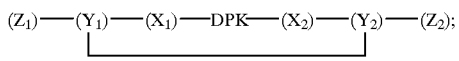

Within this formula, $X_1$, and $X_2$ are optional, and if present, are independently selected from the group consisting of amino acid residues and combinations thereof in which the residues are linked by peptide bonds, and wherein $X_1$ and $X_2$ independently range in size from 0, to 10 residues, such that the sum of residues contained within $X_1$ and $X_2$ ranges from 1 to 12; $Y_1$ and $Y_2$ are independently selected from the group consisting of amino acid residues, and wherein a covalent bond is formed between residues $Y_1$ and $Y_2$; and $Z_1$ and $Z_2$ are optional, and if present, are independently selected from the group consisting of amino acid residues and combinations thereof in which the residues are linked by peptide bonds.

Cyclic peptides may comprise any of the above CAR sequence(s). Such cyclic peptides may be used as modulating agents without modification, or may be incorporated into a modulating agent. Within the context of the present invention, underlined sequences are cyclized using any suitable method, as described herein.

Within certain embodiments, as discussed below, cyclic peptides that contain small CAR sequences (e.g., five residues, such as CDPKC (SEQ ID NO:3), without significant flanking sequences) are preferred for modulating JAM-mediated functions. Such peptides may contain an N-acetyl group and a C-amide group. Small cyclic peptides may generally be used to specifically modulate adhesion of cancer and/or other cell types by topical administration or by systemic administration, with or without linking a targeting agent to the peptide, as discussed below. Within other preferred embodiments, a cyclic peptide may contain sequences that flank the JAM CAR sequence on one or both sides, which may result in increased potency and/or specificity. Suitable flanking sequences include, but are not limited to, an endogenous sequence present in a naturally occurring JAM. To facilitate the preparation of cyclic peptides having increased potency, nuclear magnetic resonance (NMR) and computational techniques may be used to determine the conformation of a peptide that confers increased potency, as described above.

Within embodiments in which inhibition of a JAM interaction is desired, a modulating agent may contain one JAM CAR sequence, or multiple CAR sequences that are adjacent to one another (i.e., without intervening sequences) or in close proximity (i.e., separated by peptide and/or non-peptide linkers to give a distance between the JAM CAR sequences that ranges from about 0.1 to 400 nm). For example, a modulating agent with adjacent DPK sequences may comprise the peptide DPKDPK (SEQ ID NO:4). A linker may be any molecule (including peptide and/or non-peptide sequences) that does not contain a CAR sequence and that can be covalently linked to at least two peptide sequences. Using a linker, CAR sequence-containing peptides and other peptide or protein sequences may be joined end-to-end (i.e., the linker may be covalently attached to the carboxyl or amino group of each peptide sequence), and/or via side chains. One linker that can be used for such purposes is $(H_2N(CH_2)_nCO_2H)$, or derivatives thereof, where n ranges from 1 to 4. Other linkers that may be used will be apparent to those of ordinary skill in the art. Peptide and non-peptide linkers may generally be incorporated into a modulating agent using any appropriate method known in the art.

Within embodiments in which enhancement of cell adhesion mediated by a JAM is desired, a modulating agent may contain multiple JAM CAR sequences, or antibodies that specifically bind to such sequences, joined by linkers as described above. For enhancers of JAM function, the linker distance should generally be 400–10,000 nm. One linker that can be used for such purposes is $(H_2N(CH_2)_nCO_2H)_m$, or derivatives thereof, where n ranges from 1 to 10 and m ranges from 1 to 4000. For example, if glycine $(H_2NCH_2CO_2H)$ or a multimer thereof is used as a linker, each glycine unit corresponds to a linking distance of 2.45 angstroms, or 0.245 nm, as determined by calculation of its lowest energy conformation when linked to other amino acids using molecular modeling techniques. Similarly, aminopropanoic acid corresponds to a linking distance of 3.73 angstroms, aminobutanoic acid to 4.96 angstroms, aminopentanoic acid to 6.30 angstroms and amino hexanoic acid to 6.12 angstroms. Enhancement of cell adhesion may also be achieved by attachment of multiple modulating agents to a support material, as discussed further below.

A modulating agent as described herein may additionally comprise a CAR sequence for one or more different adhesion molecules (including, but not limited to, other CAMs) and/or one or more antibodies or fragments thereof that bind to such sequences. Linkers may, but need not, be used to separate such CAR sequence(s) and/or antibody sequence(s) from the JAM CAR sequence(s) and/or each other. Such modulating agents may generally be used within methods in which it is desirable to simultaneously disrupt cell adhesion mediated by multiple adhesion molecules. For cyclic peptides, additional CAR sequences may be present within the cyclic peptide ring, within a separate cyclic peptide component of the modulating agent and/or in a non-cyclic portion of the modulating agent. Antibodies and antigen-binding fragments thereof are typically present in a non-cyclic portion of the modulating agent.

As used herein, an "adhesion molecule" is any molecule that mediates cell adhesion via a receptor on the cell's surface. Adhesion molecules include cell adhesion proteins (e.g., classical cadherins, other members of the cadherin gene superfamily that are not classical cadherins (such as atypical cadherins (e.g., VE-cadherin and PB-cadherin), desmogleins (Dsg) and desmocollins (Dsc)); integrins; occludin; claudins; and members of the immunoglobulin supergene family, such as N-CAM and PECAM). Preferred CAR sequences for inclusion within a modulating agent include His-Ala-Val (HAV), which is bound by classical cadherins (Munro SB et al., 1996, *In: Cell Adhesion and Invasion in Cancer Metastasis,* P. Brodt, ed., pp.17–34 (RG Landes Company, Austin Tex.); Arg-Gly-Asp (RGD), which is bound by integrins (see Cardarelli et al., *J. Biol. Chem.* 267:23159–64, 1992); KYSFNYDGSE (SEQ ID NO:5), which is bound by N-CAM; the occludin CAR sequence LYHY (SEQ ID NO:6); and/or one or more nonclassical cadherin CAR sequences, such as the VE-cadherin CAR sequence DAE, the Dsc CAR sequences IEK, VER and IER, the Dsg CAR sequences INQ, INR and LNK; and the claudin CAR sequence IYSY (SEQ ID NO:7).

Using linkers, JAM CAR sequence-containing peptides and other peptide or protein sequences may be joined head-to-tail (i.e., the linker may be covalently attached to the carboxyl or amino group of each peptide sequence), head-to-side chain and/or tail-to-side chain. Modulating agents comprising one or more linkers may form linear or branched structures. Within one embodiment, modulating agents having a branched structure may comprise a JAM CAR sequence and an occludin CAR sequence. Alternatively, a branched structure may comprise three different CAR sequences, such as RGD, a JAM CAR sequence and HAV. Within another embodiment, modulating agents having a branched structure comprise a JAM CAR sequence, along with one or more of HAV, RGD, LYHY (SEQ ID NO:6), DAE, IEK, VER, IER, INQ, INR, IYSY (SEQ ID NO:7) and/or LNK.

Other combinations of CAR sequences are also possible. Linkers preferably produce a distance between CAR sequences between 0.1 to 10,000 nm, more preferably about 0.1–400 nm. A separation distance between recognition sites may generally be determined according to the desired function of the modulating agent, as discussed above.

The total number of CAR sequences (including JAM CAR sequence(s)), with or without other CAR sequences derived from one or more adhesion molecules) present within a modulating agent may range from 1 to a large number, such as 100, preferably from 1 to 10, and more preferably from 1 to 5. Peptide modulating agents comprising multiple CAR sequences typically contain from 6 to about 1000 amino acid residues, preferably from 6 to 50 residues. When non-peptide linkers are employed, each CAR sequence of the modulating agent is present within a peptide that generally ranges in size from 4 to 50 residues in length, preferably from 4 to 25 residues, more preferably from 4 to 16 residues and still more preferably from 4 to 15 residues.

As noted above, modulating agents may be polypeptides or salts thereof, containing only amino acid residues linked by peptide bonds, or may contain non-peptide regions, such as linkers. Peptide regions of a modulating agent may comprise residues of L-amino acids, D-amino acids, or any combination thereof. Amino acids may be from natural or non-natural sources, provided that at least one amino group and at least one carboxyl group are present in the molecule; α- and β-amino acids are generally preferred. The 20 L-amino acids commonly found in proteins are identified herein by the conventional three-letter or one-letter abbreviations, and the corresponding D-amino acids are designated by a lower case one letter symbol.

A modulating agent may also contain rare amino acids (such as 4-hydroxyproline or hydroxylysine), organic acids or amides and/or derivatives of common amino acids, such as amino acids having the C-terminal carboxylate esterified (e.g., benzyl, methyl or ethyl ester) or amidated and/or having modifications of the N-terminal amino group (e.g., acetylation or alkoxycarbonylation), with or without any of a wide variety of side-chain modifications and/or substitutions (e.g., methylation, benzylation, t-butylation, tosylation, alkoxycarbonylation, and the like). Preferred derivatives include amino acids having a C-terminal amide group. Residues other than common amino acids that may be present with a modulating agent include, but are not limited to, 2-mercaptoaniline, 2-mercaptoproline, ornithine, diaminobutyric acid, α-aminoadipic acid, m-aminomethylbenzoic acid and α,β-diaminopropionic acid.

Peptide modulating agents (and peptide portions of modulating agents) as described herein may be synthesized by methods well known in the art, including chemical synthesis and recombinant DNA methods. For modulating agents up to about 50 residues in length, chemical synthesis may be performed using solution or solid phase peptide synthesis techniques, in which a peptide linkage occurs through the direct condensation of the α-amino group of one amino acid with the α-carboxy group of the other amino acid with the elimination of a water molecule. Peptide bond synthesis by direct condensation, as formulated above, requires suppression of the reactive character of the amino group of the first and of the carboxyl group of the second amino acid. The masking substituents must permit their ready removal, without inducing breakdown of the labile peptide molecule.

In solution phase synthesis, a wide variety of coupling methods and protecting groups may be used (see Gross and Meienhofer, eds., "The Peptides: Analysis, Synthesis, Biology," Vol. 1–4 (Academic Press, 1979); Bodansky and Bodansky, "The Practice of Peptide Synthesis," 2d ed. (Springer Verlag, 1994)). In addition, intermediate purification and linear scale up are possible. Those of ordinary skill in the art will appreciate that solution synthesis requires consideration of main chain and side chain protecting groups and activation method. In addition, careful segment selection is necessary to minimize racemization during segment condensation. Solubility considerations are also a factor.

Solid phase peptide synthesis uses an insoluble polymer for support during organic synthesis. The polymer-supported peptide chain permits the use of simple washing and filtration steps instead of laborious purifications at intermediate steps. Solid-phase peptide synthesis may generally be performed according to the method of Merrifield et al., *J. Am. Chem. Soc.* 85:2149, 1963, which involves assembling a linear peptide chain on a resin support using protected amino acids. Solid phase peptide synthesis typically utilizes either the Boc or Fmoc strategy. The Boc strategy uses a 1% cross-linked polystyrene resin. The standard protecting group for α-amino functions is the tert-butyloxycarbonyl (Boc) group. This group can be removed with dilute solutions of strong acids such as 25% trifluoroacetic acid (TFA). The next Boc-amino acid is typically coupled to the amino acyl resin using dicyclohexylcarbodiimide (DCC). Following completion of the assembly, the peptide-resin is treated with anhydrous HF to cleave the benzyl ester link and liberate the free peptide. Side-chain functional groups are usually blocked during synthesis by benzyl-derived blocking groups, which are also cleaved by HF. The free peptide is then extracted from the resin with a suitable solvent, purified and characterized. Newly synthesized peptides can be purified, for example, by gel filtration, HPLC, partition chromatography and/or ion-exchange chromatography, and may be characterized by, for example, mass spectrometry or amino acid sequence analysis. In the Boc strategy, C-terminal amidated peptides can be obtained using benzhydrylamine or methylbenzhydrylamine resins, which yield peptide amides directly upon cleavage with HF.

In the procedures discussed above, the selectivity of the side-chain blocking groups and of the peptide-resin link depends upon the differences in the rate of acidolytic cleavage. Orthoganol systems have been introduced in which the side-chain blocking groups and the peptide-resin link are completely stable to the reagent used to remove the α-protecting group at each step of the synthesis. The most common of these methods involves the 9-fluorenylmethyloxycarbonyl (Fmoc) approach. Within this method, the side-chain protecting groups and the peptide-resin link are completely stable to the secondary amines used for cleaving the N-α-Fmoc group. The side-chain protection and the peptide-resin link are cleaved by mild acidolysis. The repeated contact with base makes the Merrifield resin unsuitable for Fmoc chemistry, and p-alkoxybenzyl esters linked to the resin are generally used. Deprotection and cleavage are generally accomplished using TFA.

Those of ordinary skill in the art will recognize that, in solid phase synthesis, deprotection and coupling reactions must go to completion and the side-chain blocking groups must be stable throughout the entire synthesis. In addition, solid phase synthesis is generally most suitable when peptides are to be made on a small scale.

Acetylation of the N-terminus can be accomplished by reacting the final peptide with acetic anhydride before cleavage from the resin. C-amidation is accomplished using an appropriate resin such as methylbenzhydrylamine resin using the Boc technology.

Following synthesis of a linear peptide, with or without N-acetylation and/or C-amidation, cyclization may be achieved if desired by any of a variety of techniques well known in the art. Within one embodiment, a bond may be generated between reactive amino acid side chains. For example, a disulfide bridge may be formed from a linear peptide comprising two thiol-containing residues by oxidizing the peptide using any of a variety of methods. Within one such method, air oxidation of thiols can generate disulfide linkages over a period of several days using either basic or neutral aqueous media. The peptide is used in high dilution to minimize aggregation and intermolecular side reactions. This method suffers from the disadvantage of being slow but has the advantage of only producing $H_2O$ as a side product. Alternatively, strong oxidizing agents such as $I_2$ and $K_3Fe(CN)_6$ can be used to form disulfide linkages. Those of ordinary skill in the art will recognize that care must be taken not to oxidize the sensitive side chains of Met, Tyr, Trp or His. Cyclic peptides produced by this method require purification using standard techniques, but this oxidation is applicable at acid pHs. Oxidizing agents also allow concurrent deprotection/oxidation of suitable S-protected linear precursors to avoid premature, nonspecific oxidation of free cysteine.

DMSO, unlike $I_2$ and $K_3Fe(CN)_6$, is a mild oxidizing agent which does not cause oxidative side reactions of the nucleophilic amino acids mentioned above. DMSO is miscible with $H_2O$ at all concentrations, and oxidations can be performed at acidic to neutral pHs with harmless byproducts. Methyltrichlorosilane-diphenylsulfoxide may alternatively be used as an oxidizing agent, for concurrent deprotection/oxidation of S-Acm, S-Tacm or S-t-Bu of cysteine without affecting other nucleophilic amino acids. There are no polymeric products resulting from intermolecular disulfide bond formation. Suitable thiol-containing residues for use in such oxidation methods include, but are not limited to, cysteine, β,β-dimethyl cysteine (penicillamine or Pen), β,β-tetramethylene cysteine (Tmc), β,β-pentamethylene cysteine (Pmc), β-mercaptopropionic acid (Mpr), β,β-pentamethylene-β-mercaptopropionic acid (Pmp), 2-mercaptobenzene, 2-mercaptoaniline and 2-mercaptoproline.

Within another embodiment, cyclization may be achieved by amide bond formation. For example, a peptide bond may be formed between terminal functional groups (i.e., the amino and carboxy termini of a linear peptide prior to cyclization). Within another such embodiment, the cyclic peptide comprises a D-amino acid. Alternatively, cyclization may be accomplished by linking one terminus and a residue side chain or using two side chains, with or without an N-terminal acetyl group and/or a C-terminal amide. Residues capable of forming a lactam bond include lysine, ornithine (Orn), α-amino adipic acid, m-aminomethylbenzoic acid, α,β-diaminopropionic acid, glutamate or aspartate.

Methods for forming amide bonds are well known in the art and are based on well established principles of chemical reactivity. Within one such method, carbodiimide-mediated lactam formation can be accomplished by reaction of the carboxylic acid with DCC, DIC, EDAC or DCCI, resulting in the formation of an O-acylurea that can be reacted immediately with the free amino group to complete the cyclization. The formation of the inactive N-acylurea, resulting from O→N migration, can be circumvented by converting the O-acylurea to an active ester by reaction with an N-hydroxy compound such as 1-hydroxybenzotriazole, 1-hydroxysuccinimide, 1-hydroxynorbornene carboxamide or ethyl 2-hydroximino-2-cyanoacetate. In addition to minimizing O→N migration, these additives also serve as catalysts during cyclization and assist in lowering racemization. Alternatively, cyclization can be performed using the azide method, in which a reactive azide intermediate is generated from an alkyl ester via a hydrazide. Hydrazinolysis of the terminal ester necessitates the use of a t-butyl group for the protection of side chain carboxyl functions in the acylating component. This limitation can be overcome by using diphenylphosphoryl acid (DPPA), which furnishes an azide directly upon reaction with a carboxyl group. The slow reactivity of azides and the formation of isocyanates by their disproportionation restrict the usefulness of this method. The mixed anhydride method of lactam formation is widely used because of the facile removal of reaction by-products. The anhydride is formed upon reaction of the carboxylate anion with an alkyl chloroformate or pivaloyl chloride. The attack of the amino component is then guided to the carbonyl carbon of the acylating component by the electron donating effect of the alkoxy group or by the steric bulk of the pivaloyl chloride t-butyl group, which obstructs attack on the wrong carbonyl group. Mixed anhydrides with phosphoric acid derivatives have also been successfully used. Alternatively, cyclization can be accomplished using activated esters. The presence of electron withdrawing substituents on the alkoxy carbon of esters increases their susceptibility to aminolysis. The high reactivity of esters of p-nitrophenol, N-hydroxy compounds and polyhalogenated phenols has made these "active esters" useful in the synthesis of amide bonds. The last few years have witnessed the development of benzotriazolyloxytris-(dimethylamino) phosphonium hexafluorophosphonate (BOP) and its congeners as advantageous coupling reagents. Their performance is generally superior to that of the well established carbodiimide amide bond formation reactions.

Within a further embodiment, a thioether linkage may be formed between the side chain of a thiol-containing residue and an appropriately derivatized α-amino acid. By way of example, a lysine side chain can be coupled to bromoacetic acid through the carbodiimide coupling method (DCC, EDAC) and then reacted with the side chain of any of the thiol containing residues mentioned above to form a thioether linkage. In order to form dithioethers, any two thiol containing side-chains can be reacted with dibromoethane and diisopropylamine in DMF. Examples of thiol-containing linkages are shown below:

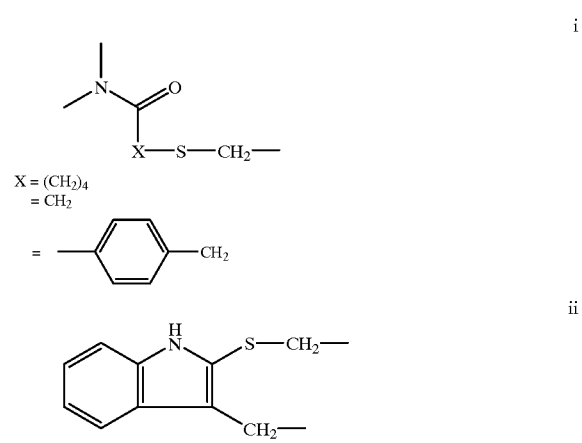

Cyclization may also be achieved using $\delta_1,\delta_{1'}$-Ditryptophan (i.e., Ac-<u>Trp-Gly-Gly-Trp</u>-OMe)(SEQ ID NO:8), as shown below:

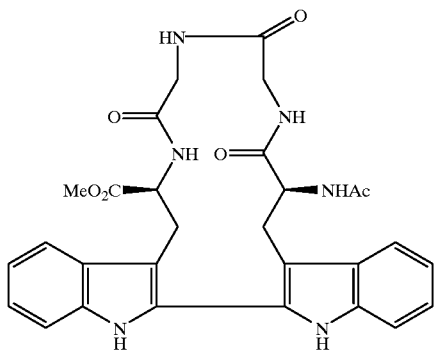

For longer modulating agents, recombinant methods are preferred for synthesis. Within such methods, all or part of a modulating agent can be synthesized in living cells, using any of a variety of expression vectors known to those of ordinary skill in the art to be appropriate for the particular host cell. Suitable host cells may include bacteria, yeast cells, mammalian cells, insect cells, plant cells, algae and other animal cells (e.g., hybridoma, CHO, myeloma). The DNA sequences expressed in this manner may encode portions of an endogenous JAM or other adhesion molecule. Such sequences may be prepared based on known cDNA or genomic sequences, or from sequences isolated by screening an appropriate library with probes designed based on known JAM sequences. Such screens may generally be performed as described in Sambrook et al., *Molecular Cloning: A Laboratory Manual,* Cold Spring Harbor Laboratories, Cold Spring Harbor, N.Y., 1989 (and references cited therein). Polymerase chain reaction (PCR) may also be employed, using oligonucleotide primers in methods well known in the art, to isolate nucleic acid molecules encoding all or a portion of an endogenous adhesion molecule. To generate a nucleic acid molecule encoding a desired modulating agent, an endogenous JAM sequence may be modified using well known techniques. For example, portions encoding one or more CAR sequences may be joined, with or without separation by nucleic acid regions encoding linkers, as discussed above. Alternatively, portions of the desired nucleic acid sequences may be synthesized using well known techniques, and then ligated together to form a sequence encoding the modulating agent.

As noted above, polynucleotides may also function as modulating agents. In general, such polynucleotides should be formulated to permit expression of a polypeptide modulating agent following administration to a mammal. Such formulations are particularly useful for therapeutic purposes, as described below. Those of ordinary skill in the art will appreciate that there are many ways to achieve expression of a polynucleotide within a mammal, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transfected cells) and/or a targeting moiety, such as a gene that encodes a ligand for a receptor on a specific target cell, to render the vector target specific. Targeting may also be accomplished using an antibody, by methods known to those of ordinary skill in the art. Other formulations for polynucleotides for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (ie., an artificial membrane vesicle). The preparation and use of such systems is well known in the art.

As noted above, instead of (or in addition to) a JAM CAR sequence, a modulating agent may comprise an antibody, or antigen-binding fragment thereof, that specifically binds to a JAM CAR sequence. As used herein, an antibody, or antigen-binding fragment thereof, is said to "specifically bind" to a JAM CAR sequence (with or without flanking amino acids) if it reacts at a detectable level with a peptide containing that sequence, and does not react detectably with peptides containing a different CAR sequence or a sequence in which the order of amino acid residues in the JAM CAR sequence and/or flanking sequence is altered. Such antibody binding properties may be assessed using an ELISA, as described by Newton et al., *Develop. Dynamics* 197:1–13, 1993.

Polyclonal and monoclonal antibodies may be raised against a JAM CAR sequence using conventional techniques. See, e.g., Harlow and Lane, *Antibodies: A Laboratory Manual,* Cold Spring Harbor Laboratory, 1988. In one such technique, an immunogen comprising the JAM CAR sequence is initially injected into any of a wide variety of mammals (e.g., mice, rats, rabbits, sheep or goats). The smaller immunogens (i.e., less than about 20 amino acids) should be joined to a carrier protein, such as bovine serum albumin or keyhole limpet hemocyanin. Following one or more injections, the animals are bled periodically. Polyclonal antibodies specific for the CAR sequence may then be purified from such antisera by, for example, affinity chromatography using the modulating agent or antigenic portion thereof coupled to a suitable solid support.

Monoclonal antibodies specific for the JAM CAR sequence may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity from spleen cells obtained from an animal immunized as described above. The spleen cells are immortalized by, for example, fusion with a myeloma cell fusion partner, preferably one that is syngeneic with the immunized animal. Single colonies are selected and their culture supernatants tested for binding activity against the modulating agent or antigenic portion thereof. Hybridomas having high reactivity and specificity are preferred.

Monoclonal antibodies may be isolated from the supernatants of growing hybridoma colonies, with or without the use of various techniques known in the art to enhance the yield. Contaminants may be removed from the antibodies by conventional techniques, such as chromatography, gel filtration, precipitation, and extraction. Antibodies having the desired activity may generally be identified using immunofluorescence analyses of tissue sections, cell or other samples where the target JAM is localized.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual,* Cold Spring Harbor Laboratory, 1988; see especially page 309) and digested by papain to yield Fab and Fc fragments. The Fab and Fc fragments may be separated by affinity chromatography on protein A bead columns (Harlow and Lane, 1988, pages 628–29).

Evaluation of Modulating Agent Activity

As noted above, modulating agents as described herein are capable of modulating JAM-mediated cell adhesion. The ability of an agent to modulate cell adhesion may generally be evaluated in vitro by assaying the effect on endothelial and/or epithelial cell adhesion or cells transfected with JAM cDNA, such as L cells (Furuse et al. *J Cell Biol.* 143:391–401, 1998), using, for example, any of a variety of immunostaining protocols and/or plating assays. In general, a modulating agent is an inhibitor of cell adhesion if contact of the test cells with the modulating agent results in a discernible disruption of cell adhesion using one or more representative assays provided herein. Modulating agents that enhance cell adhesion (e.g., agents comprising multiple JAM CAR sequences and/or linked to a support molecule or material) are considered to be modulators of cell adhesion if they are capable of promoting cell adhesion, as judged by plating assays to assess either endothelial or epithelial cell adhesion to a modulating agent attached to a support material, such as tissue culture plastic.

An initial screen for the ability to modulate one or more JAM-mediated functions may be performed by evaluating the ability of a modulating agent to bind to a JAM using any binding assay known to those of ordinary skill in the art. For example, a Pharmacia Biosensor machine may be used, as discussed in Jonsson et al., *Biotechniques* 11:520–27, 1991. For example, a modulating agent may comprise a CAR sequence that binds to a JAM. A specific example of a technology that measures the interaction of peptides with molecules can be found in Williams et al., *J. Biol Chem.* 272, 22349–22354, 1997. Alternatively, real-time BIA (Biomolecular Interaction Analysis) uses the optical phenomenon surface plasmon resonance to monitor biomolecular interactions. The detection depends upon changes in the mass concentration of macromolecules at the biospecific interface, which in turn depends upon the immobilization of test molecule or peptide (referred to as the ligand) to the surface of a Biosensor chip, followed by binding of the interacting molecule (referred to as the analyte) to the ligand. Binding to the chip is measured in real-time in arbitrary units of resonance (RU).

By way of example, surface plasmon resonance experiments may be carried out using a BIAcore X™ Biosensor (Pharmacia Ltd., BIAcore, Uppsala, Sweden). Parallel flow cells of CM 5 sensor chips may be derivatized, using the amine coupling method, with streptavidin (200 μg/ml) in 10 mM Sodium Acetate, pH 4.0, according to the manufacturer's protocol. Approximately 2100–2600 resonance units (RU) of ligand may be immobilized, corresponding to a concentration of about 2.1–2.6 ng/mm$^2$. The chips may then coated be with JAM derivatized to biotin. Any non-specifically bound protein is removed.

To determine binding, test analytes (e.g., peptides containing the JAM CAR sequence) may be placed in running buffer and passed simultaneously over test and control flow cells. After a period of free buffer flow, any analyte remaining bound to the surface may be removed with, for example, a pulse of 0.1% SDS bringing the signal back to baseline. Specific binding to the derivatized sensor chips may be determined automatically by the system by subtraction of test from control flow cell responses. In general, a modulating agent binds to a JAM at a detectable level within such as assay. The level of binding is preferably at least that observed for the full length JAM under similar conditions.

The ability of an agent to modulate cell adhesion may generally be evaluated in vivo by assessing the effect on vascular permeability utilizing the Miles assay (McClure et al., *J. Pharmacological & Toxicological Methods* 32:49–52, 1994). Briefly, a candidate modulating agent may be dissolved in phosphate buffered saline (PBS) at a concentration of 100 μg/ml. Adult rats may be given 100 μl subdermal injections of each peptide solution into their shaved backs, followed 15 minutes later by a single 250 μl injection of 1% Evans blue dissolved in PBS into their tail veins. The subdermal injection sites may be visually monitored for the appearance of blue dye. Once the dye appears (about 15 minutes after injection), each subdermal injection site may be excised, weighed, and placed in 1 ml dimethylformamide for 24 hours to extract the dye. The optical density of the dye extracts may then be determined at 620 nm. In general, the injection of 0.1 ml of modulating agent (at a concentration of 0.1 mg/ml) into the backs of rats causes an increase of dye accumulation at the injection sites of at least 50%, as compared to dye accumulation at sites into which PBS has been injected.

The effect of a modulating agent on endothelial cell adhesion may generally be evaluated using immunolocalization techniques. Human aortic endothelial cells (HAEC) may be cultured on fibronectin-coated coverslips (fibronectin may be obtained from Sigma, St. Louis, Mo.) according to the procedures of Jaffe et al., *J. Clin. Invest.* 52:2745–2756, 1973. Briefly, human endothelial cells may be maintained in EGM (endothelial cell growth medium; Clonetics, San Diego, Calif.) and used for experiments at passage 4. Confluent cultures of HAEC may be exposed to either a candidate modulating agent (final concentration 100 μg/ml EGM), or EGM alone for 1 hour. The cells are then be fixed for 30 minutes at 4° C. in 95% ethanol, followed by fixation in acetone for 1 minute at 4° C. (Furuse et al.,*J. Cell Biol.* 123:1777–1788, 1993). After fixation, the cells may be probed with either mouse anti-VE-cadherin antibodies (Hemeris, Sassenage, France; diluted 1:250 in 0.1% dried skim milk powder dissolved in PBS), or anti-JAM antibodies (prepared as described by Martin-Padura et al., *J. Cell. Biol.* 142:117–127, 1998) diluted in 0.1% dried skim milk powder dissolved in PBS) for 1 hour at 37° C. The cells may then be washed with 0.1% dried skim milk powder dissolved in PBS (three washes, 5 minutes/wash), and probed with secondary antibodies (donkey anti-mouse Cy3, or donkey anti-rat Cy5 diluted 1:250 in 0.1% dried skim milk powder dissolved in PBS; Jackson Immunoresearch Laboratories Inc., Westgrove, Pa.) for 1 hour at 37° C. The cells may then be washed again with in 0.1% dried skim milk powder dissolved in PBS and mounted in a solution composed of 50% glycerol and 50% PBS to which phenylenediamine (Sigma, St. Louis, Mo.) has been added to a final concentration of 1 mg/ml. The sample may then be analyzed using a Bio-Rad MRC 1000 confocal microscope with Laser Sharp software version 2.1T (Bio-Rad, Hercules, Calif.). In general, 0.1 mg/ml of modulating agent results in the appearance of intercellular gaps within the monolayer cultures and a decrease of at least 50% in the surface expression of JAM and VE-cadherin, as compared to monolayer cultures that were not exposed to the modulating agent.

Another such assay evaluates leukocyte (e.g., monocyte) transmigration through an endothelial cell layer (see Martin-Padura et al., *J. Cell. Biol.* 142:117–127, 1998). Human umbilical vein endothelial cells for use in such assays may be cultured using standard techniques, such as in 24 well format 8 mm inserts (Falcon). A fresh 24 well plate may be filled with 1 mL HBSS (Hanks balanced salts solution) in each of the lower wells. In all wells, a chemoattractant is then added (e.g., IL-8 added to a final concentration of 1 μM). Medium is removed from the upper well and HBSS plus modulating agent are added to the upper wells of the insert plates (e.g., at 200 μg/ml) and pre-incubated (e.g., for 1 hour). Leukocytes may be labeled by, for example, incubation with 30 μl of $^{51}$Cr (5 mCi/5 ml, NEN, Natick, Mass.) for 1 hour at 37° C., with 3 washing steps with HBSS. The concentration of the leukocyte suspension may be adjusted to about 2×10$^7$ cells/mL before starting the assay. This leukocyte suspension (e.g., 50 mL) is added to the upper well and the inserts incubated in the new chemoattractant supplemented tray for 60 minutes. The inserts may then be removed and discarded. The contents from each well are aspirated and placed in a separate gamma counter tube. Wells may be washed twice with 1N NaOH, and the wash added to the same tube. Samples may be read by gamma counting for $^{51}$Cr and may be expressed as a percentage of the total leukocytes added to each upper well chamber. In general, 200 μg/ml modulating agent should result in an increase in transmigration by at least 50%.

Within certain cell adhesion assays, the addition of a modulating agent to cells that express JAM results in disruption of cell adhesion. A "JAM-expressing cell," as used herein, may be any type of cell that expresses JAM on the cell surface at a detectable level, using standard techniques such as immunocytochemical protocols (e.g., Blaschuk and Farookhi, *Dev. Biol.* 136:564–567, 1989). JAM-expressing cells include endothelial and epithelial cells, as well as megakaryocytes and mesothelial cells. For example, such cells may be plated under standard conditions that, in the absence of modulating agent, permit cell adhesion. In the presence of modulating agent (e.g., 100 μg/mL), disruption of cell adhesion may be determined visually within 24 hours, by observing retraction of the cells from one another.

Within another such assay, the effect of a modulating agent on normal rat kidney (NRK) cells may be evaluated. According to a representative procedure, NRK cells (ATCC #1571-CRL) may be plated at 10–20,000 cells per 35 mm tissue culture flasks containing DMEM with 10% FCS and sub-cultured periodically (Laird et al., *J. Cell Biol.* 131:1193–1203, 1995). Cells may be harvested and replated in 35 mm tissue culture flasks containing 1 mm coverslips and incubated until 50–65% confluent (24–36 hours). At this time, coverslips may be transferred to a 24-well plate, washed once with fresh DMEM and exposed to modulating agent at a concentration of, for example, 0.1 mg/mL for 24 hours. Fresh modulating agent may then be added, and the cells left for an additional 24 hours. Cells may be fixed with 100% methanol for 10 minutes and then washed three times with PBS. Coverslips may be blocked for 1 hour in 2% BSA/PBS and incubated for a further 1 hour in the presence of anti-JAM antibody and mouse anti-E-cadherin antibody (Transduction Labs, 1:250 dilution). Primary and secondary antibodies may be diluted in 2% BSA/PBS. Following incubation in the primary antibody, coverslips may be washed three times for 5 minutes each in PBS and incubated for 1 hour with donkey anti-mouse Cy3 and donkey anti-rabbit Cy5 (Jackson Immunoresearch Laboratories Inc., Westgrove, Pa.) for 1 hour at 37° C. Following further washes in PBS (3×5 min) coverslips can be mounted and viewed by confocal microscopy.

In the absence of modulating agent, NRK cells form characteristic tightly adherent monolayers with a cobblestone morphology in which cells display a polygonal shape. NRK cells that are treated with a modulating agent that disrupts JAM-mediated cell adhesion may assume a non-polygonal and elongated morphology (i.e., a fibroblast-like shape) within 48 hours of treatment with 0.1 mg/mL of modulating agent. Gaps appear in confluent cultures of such cells. In addition, 0.1 mg/mL of such a modulating agent reproducibly induces a readily apparent reduction in cell surface staining of JAM and E-cadherin, as judged by immunofluorescence microscopy (Laird et al., *J. Cell Biol.* 131:1193–1203, 1995), preferably at least 75% within 48 hours.

A third cell adhesion assay involves evaluating the effect of a modulating agent on permeability of adherent endothelial cell monolayers. The effects of a modulating agent on the permeability of endothelial cell monolayers may be assessed utilizing the protocols of Ehringer et al., *J. Cell. Physiol.* 167:562–569, 1996. HAEC can be seeded onto inserts in 24-well plates (Becton-Dickenson, Franklin Lake, N.J.) and cultured in EGM. Confluent cell monolayers may be exposed to either modulating agent (final concentration 100 μg/ml EGM), or EGM alone for 1 hour. The inserts may then be transferred to 24-chamber plates (Becton-Dickenson) for permeability assays. Perfusate (0.5% bovine serum albumin, fraction V (Sigma) dissolved in 15 mM HEPES, pH 7.4) and FITC-Dextran (50 μg/ml HEPES buffer; MW 12 kDa; Sigma) may be added to each well (1 ml/well and 50 μl/well, respectively), and the cells incubated at 37° C. for 30 min. Aliquots of 100 μl may then be removed from the lower chamber and the optical density of the solution determined at a wavelength of 450 nm. In general, the presence of 100 μg/mL modulating agent that enhances the permeability of endothelial cell monolayers results in a statistically significant increase in the amount of marker in the receptor compartment after 1 hour.

Alternatively, cells that do not naturally express a JAM may be used within such assays. Such cells may be stably transfected with a polynucleotide (e.g., a cDNA) encoding a JAM of interest, such that the JAM is expressed on the surface of the cell. Transfection of cells for use in cell adhesion assays may be performed using standard techniques and published JAM sequences. Expression of the JAM may be confirmed by assessing adhesion of the transfected cells, in conjunction with immunocytochemical techniques using antibodies directed against the JAM of interest. The stably transfected cells that aggregate, as judged by light microscopy, following transfection express sufficient levels of the JAM. Preferred cells for use in such assays include L cells, which do not detectably adhere in the absence of transfection (Nagafuchi et al., *Nature* 329:341–343, 1987). Following transfection of L cells with a cDNA encoding a JAM, cell adhesion may be observed (Furuse et al *J Cell Biol.* 143:391–401, 1998). Modulating agents that detectably inhibit such aggregation may be used to modulate functions mediated by the JAM. Such assays have been used for numerous nonclassical cadherins including OB-cadherin (Okazaki et al., *J. Biol. Chem.* 269:12092–98, 1994), cadherin-5 (Breier et al., *Blood* 87:630–641, 1996), cadherin-6 (Mbalaviele et al., *J. Cell. Biol.* 141:1467–1476, 1998), cadherin-8 (Kido et al., *Genomics* 48:186–194, 1998), cadherin-15 (Shimoyama et al., *J. Biol. Chem.* 273:10011–10018, 1998), PB-cadherin (Sugimoto et al., *J. Biol. Chem.* 271:11548–11556, 1996), LI-cadherin (Kreft et al., *J. Cell. Biol.* 136:1109–1121, 1997), protocadherin 42 and 43 (Sano et al., *EMBO J.* 12:2249–2256, 1993) and desmosomal cadherins (Marcozzi et al., *J. Cell. Sci.* 111:495–509, 1998). It will be apparent to those of ordinary skill in the art that assays may be performed in a similar manner for JAMs. In general, a modulating agent that is derived from a particular JAM CAR sequence (i.e., comprises such a CAR sequence, or an analog or mimetic thereof, or an antibody that specifically recognizes such a CAR sequence) and that modulates adhesion of a cell that expresses the same JAM is considered to modulate a function mediated by the JAM.

Yet another assay evaluates the effect of a modulating agent on the electrical resistance across a monolayer of cells. For example, Madin Darby canine kidney (MDCK) cells can be exposed to the modulating agent dissolved in medium (e.g., at a final concentration of 0.5 mg/ml for a period of 24 hours). The effect on electrical resistance can be measured using standard techniques. This assay evaluates the effect of a modulating agent on tight junction formation in epithelial cells. In general, the presence of 500 μg/mL modulating agent should result in a statistically significant decrease in electrical resistance after 24 hours.

Modulating Agent Modification and Formulations

A modulating agent as described herein may, but need not, be linked to one or more additional molecules. In particular, as discussed below, it may be beneficial for certain applications to link multiple modulating agents (which may, but need not, be identical) to a support material, such as a single molecule (e.g., keyhole limpet hemocyanin) or a solid support, such as a polymeric matrix (which may be formulated as a membrane or microstructure, such as an ultra thin film), a container surface (e.g., the surface of a tissue culture plate or the interior surface of a bioreactor), or a bead or other particle, which may be prepared from a variety of materials including glass, plastic or ceramics. For certain applications, biodegradable support materials are preferred, such as cellulose and derivatives thereof, collagen, spider silk or any of a variety of polyesters (e.g., those derived from hydroxy acids and/or lactones) or sutures (see U.S. Pat. No. 5,245,012). Within certain embodiments, modulating agents and molecules comprising other CAR sequence(s) (e.g., an HAV sequence) may be attached to a support such as a polymeric matrix, preferably in an alternating pattern.

Suitable methods for linking a modulating agent to a support material will depend upon the composition of the support and the intended use, and will be readily apparent to those of ordinary skill in the art. Attachment may generally be achieved through noncovalent association, such as adsorption or affinity or, preferably, via covalent attachment (which may be a direct linkage between a modulating agent and functional groups on the support, or may be a linkage by way of a cross-linking agent). Attachment of a modulating agent by adsorption may be achieved by contact, in a suitable buffer, with a solid support for a suitable amount of time. The contact time varies with temperature, but is generally between about 5 seconds and 1 day, and typically between about 10 seconds and 1 hour.

Covalent attachment of a modulating agent to a molecule or solid support may generally be achieved by first reacting the support material with a bifunctional reagent that will also react with a functional group, such as a hydroxyl, thiol, carboxyl, ketone or amino group, on the modulating agent. For example, a modulating agent may be bound to an appropriate polymeric support or coating using benzoquinone, by condensation of an aldehyde group on the support with an amine and an active hydrogen on the modulating agent or by condensation of an amino group on the support with a carboxylic acid on the modulating agent. A preferred method of generating a linkage is via amino groups using glutaraldehyde. A modulating agent may be linked to cellulose via ester linkages. Similarly, amide linkages may be suitable for linkage to other molecules such as keyhole limpet hemocyanin or other support materials. Multiple modulating agents and/or molecules comprising other CAR sequences may be attached, for example, by random coupling, in which equimolar amounts of such molecules are mixed with a matrix support and allowed to couple at random.

Although modulating agents as described herein may preferentially bind to specific tissues or cells, and thus may be sufficient to target a desired site in vivo, it may be beneficial for certain applications to include an additional targeting agent. Accordingly, a targeting agent may also, or alternatively, be linked to a modulating agent to facilitate targeting to one or more specific tissues. As used herein, a "targeting agent," may be any substance (such as a compound or cell) that, when linked to a modulating agent enhances the transport of the modulating agent to a target tissue, thereby increasing the local concentration of the modulating agent. Targeting agents include antibodies or fragments thereof, receptors, ligands and other molecules that bind to cells of, or in the vicinity of, the target tissue. Known targeting agents include serum hormones, antibodies against cell surface antigens, lectins, adhesion molecules, tumor cell surface binding ligands, steroids, cholesterol, lymphokines, fibrinolytic enzymes and those drugs and proteins that bind to a desired target site. For example, in receptor-mediated delivery, a modulating agent may be linked to a ligand that recognizes a specific receptor on the surface of a target cell. In certain instances, modulating agent is released within the cell following cleavage with intracellular enzymes. Among the many monoclonal antibodies that may serve as targeting agents are anti-TAC, or other interleukin-2 receptor antibodies; 9.2.27 and NR-ML-05, reactive with the 250 kilodalton human melanoma-associated proteoglycan; and NR-LU-10, reactive with a pancarcinoma glycoprotein. An antibody targeting agent may be an intact (whole) molecule, a fragment thereof, or a functional equivalent thereof Examples of antibody fragments are F(ab')2, -Fab', Fab and F[v] fragments, which may be produced by conventional methods or by genetic or protein engineering. Linkage is generally covalent and may be achieved by, for example, direct condensation or other reactions, or by way of bi- or multi-functional linkers.

For certain embodiments, it may be beneficial to also, or alternatively, link a drug to a modulating agent. As used herein, the term "drug" refers to any bioactive agent intended for administration to a mammal to prevent or treat a disease or other undesirable condition. Drugs include hormones, growth factors, proteins, peptides and other compounds. The use of certain specific drugs within the context of the present invention is discussed below.

Modulating agents as described herein may be present within a pharmaceutical composition. A pharmaceutical composition comprises one or more modulating agents in combination with one or more pharmaceutically or physiologically acceptable carriers, diluents or excipients. Such compositions may comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Within yet other embodiments, compositions of the present invention may be formulated as a lyophilizate. One or more modulating agents (alone or in combination with a targeting agent and/or drug) may, but need not, be encapsulated within liposomes using well known technology. Compositions of the present invention may be formulated for any appropriate manner of administration, including for example, topical, oral, nasal, intravenous, intracranial, intraperitoneal, subcutaneous, or intramuscular administration.

For certain embodiments, as discussed below, a pharmaceutical composition may further comprise a modulator of cell adhesion that is mediated by one or more molecules other than JAM. Such modulators may generally be prepared as described above, except that one or more non-JAM CAR sequences and/or antibodies thereto are substituted for the JAM CAR sequence. Such compositions are particularly useful for situations in which it is desirable to inhibit cell adhesion mediated by multiple cell adhesion molecules, such as other members of the cadherin gene superfamily (e.g., classical cadherins such as E-cadherin and/or nonclassical cadherins such as VE-cadherin, Dsg and Dsc); integrins; claudins; and members of the immunoglobulin supergene family, such as N-CAM and PECAM. Preferred CAR sequences for use within such a modulator include HAV, RGD, DDK, EEY, EAQ (OB-cads), DAE (VE-cad), IEK, VER, IER, INQ, INR and/or LNK. Also preferred is the occludin CAR sequence LYHY (SEQ ID NO:6) and the claudin CAR sequence IYSY (SEQ ID NO:7).

A pharmaceutical composition may also, or alternatively, contain one or more drugs, which may be linked to a modulating agent or may be free within the composition. Virtually any drug may be administered in combination with a modulating agent as described herein, for a variety of purposes as described below. Examples of types of drugs that may be administered with a modulating agent include analgesics, anesthetics, antianginals, antifungals, antibiotics, anticancer drugs (e.g., taxol or mitomycin C), antiinflammatories (e.g., ibuprofen and indomethacin), anthelmintics, antidepressants, antidotes, antiemetics, antihistamines, antihypertensives, antimalarials, antimicrotubule agents (e.g., colchicine or vinca alkaloids), antimigraine agents, antimicrobials, antiphsychotics, antipyretics, antiseptics, anti-signaling agents (e.g., protein kinase C inhibitors or inhibitors of intracellular calcium mobilization), antiarthritics, antithrombin agents, antituberculotics, antitussives, antivirals, appetite suppressants, cardioactive drugs, chemical dependency drugs, cathartics, chemotherapeutic agents, coronary, cerebral or peripheral vasodilators, contraceptive agents, depressants, diuretics, expectorants, growth factors, hormonal agents, hypnotics, immunosuppression agents, narcotic antagonists, parasympathomimetics, sedatives, stimulants, sympathomimetics, toxins (e.g., cholera toxin), tranquilizers and urinary antiinfectives.

For imaging purposes, any of a variety of diagnostic agents may be incorporated into a pharmaceutical composition, either linked to a modulating agent or free within the composition. Diagnostic agents include any substance administered to illuminate a physiological function within a patient, while leaving other physiological functions generally unaffected. Diagnostic agents include metals, radioactive isotopes and radioopaque agents (e.g., gallium, technetium, indium, strontium, iodine, barium, bromine and phosphorus-containing compounds), radiolucent agents, contrast agents, dyes (e.g., fluorescent dyes and chromophores) and enzymes that catalyze a colorimetric or fluorometric reaction. In general, such agents may be attached using a variety of techniques as described above, and may be present in any orientation.

The compositions described herein may be administered as part of a sustained release formulation (i.e., a formulation such as a capsule or sponge that effects a slow release of modulating agent following administration). Such formulations may generally be prepared using well known technology and administered by, for example, oral, rectal or subcutaneous implantation, or by implantation at the desired target site. Sustained-release formulations may contain a modulating agent dispersed in a carrier matrix and/or contained within a reservoir surrounded by a rate controlling membrane (see, e.g., European Patent Application 710,491 A). Carriers for use within such formulations are biocompatible, and may also be biodegradable; preferably the formulation provides a relatively constant level of modulating agent release. The amount of modulating agent contained within a sustained release formulation depends upon the site of implantation, the rate and expected duration of release and the nature of the condition to be treated or prevented.

Pharmaceutical compositions of the present invention may be administered in a manner appropriate to the disease to be treated (or prevented). Appropriate dosages and a suitable duration and frequency of administration will be determined by such factors as the condition of the patient, the type and severity of the patient's disease and the method of administration. In general, an appropriate dosage and treatment regimen provides the modulating agent(s) in an amount sufficient to provide therapeutic and/or prophylactic benefit. Within particularly preferred embodiments of the invention, a modulating agent or pharmaceutical composition as described herein may be administered at a dosage ranging from 0.001 to 50 mg/kg body weight, preferably from 0.1 to 20 mg/kg, on a regimen of single or multiple daily doses. For topical administration, a cream typically comprises an amount of modulating agent ranging from 0.00001% to 1%, preferably from 0.0001% to 0.2% and more preferably from 0.01% to 0.1%. Fluid compositions typically contain an amount of modulating agent ranging from 10 ng/ml to 5 mg/ml, preferably from 10 $\mu$g to 2 mg/mL. Appropriate dosages may generally be determined using experimental models and/or clinical trials. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

Modulating Agent Methods of Use

In general, the modulating agents and compositions described herein may be used for modulating the adhesion of JAM-expressing cells in vitro and/or in vivo, preferably in a mammal such as a human, by contacting the JAM-expressing cell with the modulating agent. As noted above, modulating agents for purposes that involve the disruption of JAM-mediated cell adhesion may comprise a JAM CAR sequence, multiple JAM CAR sequences in close proximity and/or an antibody (or an antigen-binding fragment thereof) that recognizes the JAM CAR sequence. When it is desirable to also disrupt cell adhesion mediated by other adhesion molecules, a modulating agent may additionally comprise one or more CAR sequences bound by such adhesion molecules (and/or antibodies or fragments thereof that bind such sequences), preferably separated from each other and from the JAM CAR sequence by linkers. As noted above, such linkers may or may not comprise one or more amino acids. For enhancing cell adhesion, a modulating agent may contain multiple JAM CAR sequences or antibodies (or fragments), preferably separated by linkers, and/or may be linked to a single molecule or to a support material as described above. When it is desirable to also enhance cell adhesion mediated by other adhesion molecules, a modulating agent may additionally comprise one or more CAR sequences bound by such adhesion molecules (and/or antibodies or fragments thereof that bind such sequences), preferably separated from each other and from the JAM CAR sequence by linker.

Certain methods involving the disruption of cell adhesion as described herein have an advantage over prior techniques in that they permit the passage of molecules that are large and/or charged across barriers of JAM-expressing cells. As described in greater detail below, modulating agents as described herein may also be used to disrupt or enhance cell adhesion in a variety of other contexts. Within each of the methods described herein, one or more modulating agents may generally be administered alone, or within a pharmaceutical composition. In each specific method described herein, as noted above, a targeting agent may be employed to increase the local concentration of modulating agent at the target site.

Within certain aspects, the present invention provides methods for modulating monocyte traffic through endothelial cells. Such cells may, but need not, be within a mammal. In general, a modulating agent that disrupts JAM-mediated cell adhesion increases monocyte traffic. In one particularly preferred embodiment, a modulating agent for use within such methods is capable of disrupting cell adhesion mediated by multiple adhesion molecules. Alternatively, a separate modulator of non-JAM-mediated cell adhesion may be administered in conjunction with the modulating agent(s), either within the same pharmaceutical composition or separately.

The present invention provides, within certain aspects, methods for increasing vasopermeability in a mammal by administering one or more modulating agents or pharmaceutical compositions. Endothelial cell adhesion may be disrupted by linear and cyclic peptides containing a JAM CAR sequence. Within blood vessels, endothelial cell adhesion results in decreased vascular permeability. Accordingly, modulating agents that disrupt JAM-mediated cell adhesion as described herein, can increase vascular permeability and thus may facilitate drug delivery to previously inaccessible tissues, such as the brain. In one particularly preferred embodiment, a modulating agent for use within such methods is capable of disrupting cell adhesion mediated by multiple adhesion molecules. For example, a single branched modulating agent (or multiple agents linked to a single molecule or support material) may disrupt JAM, occludin, claudin and cadherin mediated cell adhesion, thereby disrupting tight junctions and adherens junctions. Multi-functional modulating agents comprising a JAM CAR sequence joined to the cadherin CAR sequence HAV, the VE-cadherin CAR sequence DAE, the claudin CAR sequence IYSY (SEQ ID NO:7) and the occludin CAR sequence LYHY (SEQ ID NO:6), preferably by a linker, are also preferred. Alternatively, a separate modulator of non-JAM-mediated cell adhesion may be administered in conjunction with the modulating agent(s), either within the same pharmaceutical composition or separately. Preferred antibody modulating agents that may be used in conjunction with the JAM modulating agents include Fab fragments directed against an N-cadherin CAR sequence such as FHLRAHAVDINGNQV-NH$_2$ (SEQ ID NO:9), a VE-cadherin CAR sequence such as VFRVDAETG-NH$_2$ (SEQ ID NO:10), a claudin CAR sequence such as WKIYSYAG-NH$_2$ (SEQ ID NO:11), an occludin CAR sequence such as QYLYHYCVVD-NH$_2$ (SEQ ID NO:12) or an OB-cadherin CAR sequence such as IFVIDDKSG-NH$_2$ (SEQ ID NO:13).

Within certain embodiments, preferred modulating agents for use within such methods include peptides capable of decreasing both endothelial and tumor cell adhesion. Such modulating agents may be used to facilitate the penetration of anti-tumor therapeutic or diagnostic agents (e.g., monoclonal antibodies) through endothelial cell permeability barriers and tumor barriers. In one particularly preferred embodiment, a modulating agent is capable of disrupting cell adhesion mediated by multiple adhesion molecules. For example, a single branched modulating agent (or multiple agents linked to a single molecule or support material) may disrupt JAM, occludin, claudin, classical cadherin, integrin, and nonclassical cadherin (e.g., Dsc and/or Dsg) mediated cell adhesion, thereby disrupting tight junctions, adherens junctions, focal contacts and desmosomes. Multifunctional modulating agents comprising a JAM CAR sequence linked to one or more of the classical cadherin CAR sequence HAV; the sequence RGD, which is bound by integrins; the sequence LYHY (SEQ ID NO:6), which is bound by occludin, the sequence IYSY (SEQ ID NO:7) which is bound by claudins and/or a nonclassical cadherin CAR sequence, such as a VE-cadherin CAR sequence DAE, a Dsc CAR sequence (IEK, VER or IER) and/or a Dsg CAR sequence (INQ, INR or LNK), may be used to disrupt cell adhesion. Alternatively, a separate modulator of non-JAM-mediated cell adhesion may be administered in conjunction with the modulating agent(s), either within the same pharmaceutical composition or separately. Preferred antibody modulating agents that may be used in conjunction with the JAM modulating agents include Fab fragments directed against either an N-cadherin CAR sequence such as FHLRAHAVDINGNQV-NH$_2$ (SEQ ID NO:9), an E-cadherin CAR sequence such as LFSHAVSSNG-NH$_2$ (SEQ ID NO:14), an occludin CAR sequence such as QYLYHYCVVD-NH$_2$ (SEQ ID NO:12), a VE-cadherin CAR sequence such as VFRVDAETG-NH$_2$ (SEQ ID NO:10), a claudin CAR sequence such as WKIYSYAG-NH$_2$ (SEQ ID NO:11) or an OB-cadherin CAR sequence, such as IFVIDDKSG-NH$_2$ (SEQ ID NO:13).

Treatment with a modulating agent may be appropriate, for example, prior to administration of an anti-tumor therapeutic or diagnostic agent (e.g., a monoclonal antibody or other macromolecule), an antimicrobial agent or an anti-inflammatory agent, in order to increase the concentration of such agents in the vicinity of the target tumor, organism or inflammation without increasing the overall dose to the patient. Modulating agents for use within such methods may be linked to a targeting agent to further increase the local concentration of modulating agent, although systemic administration of a vasoactive agent even in the absence of a targeting agent increases the perfusion of certain tumors relative to other tissues. Suitable targeting agents include antibodies and other molecules that specifically bind to tumor cells or to components of structurally abnormal blood vessels. For example, a targeting agent may be an antibody that binds to a fibrin degradation product or a cell enzyme such as a peroxidase that is released by granulocytes or other cells in necrotic or inflamed tissues.

Administration via intravenous injection or transdermal administration is generally preferred. Effective dosages are generally sufficient to increase localization of a subsequently administered diagnostic or therapeutic agent to an extent that improves the clinical efficacy of therapy of accuracy of diagnosis to a statistically significant degree. Comparison may be made between treated and untreated tumor host animals to whom equivalent doses of the diagnostic or therapeutic agent are administered. In general, dosages range as described above.

Within certain aspects, methods are provided in which cell adhesion is diminished. In one such aspect, the present invention provides methods for reducing unwanted cellular adhesion in a mammal by administering a modulating agent as described herein. Unwanted cellular adhesion can occur, for example, between tumor cells, between tumor cells and normal cells or between normal cells as a result of surgery, injury, chemotherapy, disease, inflammation or other condition jeopardizing cell viability or function. Certain preferred modulating agents for use within such methods comprise one or more of the JAM CAR sequences provided herein. In one particularly preferred embodiment, a modulating agent is further capable of disrupting cell adhesion mediated by multiple adhesion molecules. Such an agent may comprise, in addition to one or more JAM CAR sequences, CAR sequences such as the classical cadherin CAR sequence HAV sequence, an RGD sequence, which is bound by integrins; an IYSY (SEQ ID NO:7) sequence which is bound by claudins and/or the occludin CAR sequence LYHY (SEQ ID NO:6), preferably separated from the JAM CAR sequence via a linker. Alternatively, separate modulators of cell adhesion mediated by other adhesion molecules may be administered in conjunction with the modulating agent(s), either within the same pharmaceutical composition or separately.

Topical administration of the modulating agent(s) is generally preferred, but other means may also be employed. Preferably, a fluid composition for topical administration (comprising, for example, physiological saline) comprises an amount of modulating agent as described above, and more preferably from 10 μg/mL to 1 mg/mL. Creams may generally be formulated as described above. Topical administration in the surgical field may be given once at the end of surgery by irrigation of the wound or as an intermittent or continuous irrigation with the use of surgical drains in the post-operative period or by the use of drains specifically inserted in an area of inflammation, injury or disease in cases where surgery does not need to be performed. Alternatively, parenteral or transcutaneous administration may be used to achieve similar results.

Within another such aspect, methods are provided for enhancing the delivery of a drug through the skin of a mammal. Transdermal delivery of drugs is a convenient and non-invasive method that can be used to maintain relatively constant blood levels of a drug. In general, to facilitate drug delivery via the skin, it is necessary to perturb adhesion between the epithelial cells (keratinocytes) and the endothelial cells of the microvasculature. Using currently available techniques, only small, uncharged molecules may be delivered across skin in vivo. The methods described herein are not subject to the same degree of limitation. Accordingly, a wide variety of drugs may be transported across the epithelial and endothelial cell layers of skin, for systemic or topical administration. Such drugs may be delivered to melanomas or may enter the blood stream of the mammal for delivery to other sites within the body.

To enhance the delivery of a drug through the skin, a modulating agent as described herein and a drug are contacted with the skin surface. Within certain embodiments, multifunctional modulating agents comprising a JAM CAR sequence linked to one or more of the classical cadherin CAR sequence HAV; the sequence RGD which is bound by integrins; the sequence IYSY (SEQ ID NO:7) which is bound by claudins; the sequence LYHY (SEQ ID NO:6) which is bound by occludin and/or a nonclassical cadherin CAR sequence, such as a VE-cadherin CAR sequence DAE, a Dsc CAR sequence (IEK, VER or IER) and/or a Dsg CAR sequence (INQ INR or LNK), may also be used to disrupt cell adhesion. Alternatively, a separate modulator of non-JAM-mediated cell adhesion may be administered in conjunction with the modulating agent(s), either within the same pharmaceutical composition or separately. Contact may be achieved by direct application of the modulating agent, generally within a composition formulated as a cream or gel, or using any of a variety of skin contact devices for transdermal application (such as those described in European Patent Application No. 566,816 A; U.S. Pat. Nos. 5,613,958; 5,505,956). A skin patch provides a convenient method of administration (particularly for slow-release formulations). Such patches may contain a reservoir of modulating agent and drug separated from the skin by a membrane through which the drug diffuses. Within other patch designs, the modulating agent and drug may be dissolved or suspended in a polymer or adhesive matrix that is then placed in direct contact with the patient's skin. The modulating agent and drug may then diffuse from the matrix into the skin. Modulating agent(s) and drug(s) may be contained within the same composition or skin patch, or may be separately administered, although administration at the same time and site is preferred. In general, the amount of modulating agent administered via the skin varies with the nature of the condition to be treated or prevented, but may vary as described above. Such levels may be achieved by appropriate adjustments to the device used, or by applying a cream formulated as described above. Transfer of the drug across the skin and to the target tissue may be predicted based on in vitro studies using, for example, a Franz cell apparatus, and evaluated in vivo by appropriate means that will be apparent to those of ordinary skill in the art. As an example, monitoring of the serum level of the administered drug over time provides an easy measure of the drug transfer across the skin.

Transdermal drug delivery as described herein is particularly useful in situations in which a constant rate of drug delivery is desired, to avoid fluctuating blood levels of a drug. For example, morphine is an analgesic commonly used immediately following surgery. When given intermittently in a parenteral form (intramuscular, intravenous), the patient usually feels sleepy during the first hour, is well during the next 2 hours and is in pain during the last hour because the blood level goes up quickly after the injection and goes down below the desirable level before the 4 hour interval prescribed for re-injection is reached. Transdermal administration as described herein permits the maintenance of constant levels for long periods of time (e.g., days), which allows adequate pain control and mental alertness at the same time. Insulin provides another such example. Many diabetic patients need to maintain a constant baseline level of insulin which is different from their needs at the time of meals. The baseline level may be maintained using transdermal administration of insulin, as described herein. Antibiotics may also be administered at a constant rate, maintaining adequate bactericidal blood levels, while avoiding the high levels that are often responsible for the toxicity (e.g., levels of gentamycin that are too high typically result in renal toxicity).

Drug delivery by the methods of the present invention also provide a more convenient method of drug administration. For example, it is often particularly difficult to administer parenteral drugs to newborns and infants because of the difficulty associated with finding veins of acceptable caliber to catheterize. However, newborns and infants often have a relatively large skin surface as compared to adults. Transdermal drug delivery permits easier management of such patients and allows certain types of care that can presently be given only in hospitals to be given at home. Other patients who typically have similar difficulties with venous catheterization are patients undergoing chemotherapy or patients on dialysis. In addition, for patients undergoing prolonged therapy, transdermal administration as described herein is more convenient than parenteral administration.

Transdermal administration as described herein also allows the gastrointestinal tract to be bypassed in situations where parenteral uses would not be practical. For example, there is a growing need for methods suitable for administration of therapeutic small peptides and proteins, which are typically digested within the gastrointestinal tract. The methods described herein permit administration of such compounds and allow easy administration over long periods of time. Patients who have problems with absorption through their gastrointestinal tract because of prolonged ileus or specific gastrointestinal diseases limiting drug absorption may also benefit from drugs formulated for transdermal application as described herein.

Further, there are many clinical situations where it is difficult to maintain compliance. For example, patients with mental problems (e.g., patients with Alzheimer's disease or psychosis) are easier to manage if a constant delivery rate of drug is provided without having to rely on their ability to take their medication at specific times of the day. Also patients who simply forget to take their drugs as prescribed are less likely to do so if they merely have to put on a skin patch periodically (e.g., every 3 days). Patients with diseases that are without symptoms, like patients with hypertension, are especially at risk of forgetting to take their medication as prescribed.

For patients taking multiple drugs, devices for transdermal application such as skin patches may be formulated with combinations of drugs that are frequently used together. For example, many heart failure patients are given digoxin in combination with furosemide. The combination of both drugs into a single skin patch facilitates administration, reduces the risk of errors (taking the correct pills at the appropriate time is often confusing to older people), reduces the psychological strain of taking "so many pills," reduces skipped dosage because of irregular activities and improves compliance.

The methods described herein are particularly applicable to humans, but also have a variety of veterinary uses, such as the administration of growth factors or hormones (e.g., for fertility control) to an animal.

As noted above, a wide variety of drugs may be administered according to the methods provided herein. Some examples of drug categories that may be administered transdermally include anti-inflammatory drugs (e.g., in arthritis and in other condition) such as all NSAID, indomethacin, prednisone, etc.; analgesics (especially when oral absorption is not possible, such as after surgery, and when parenteral administration is not convenient or desirable), including morphine, codeine, Demerol, acetaminophen and combinations of these (e.g., codeine plus acetaminophen); antibiotics such as Vancomycin (which is not absorbed by the GI tract and is frequently given intravenously) or a combination of INH and Rifampicin (e.g., for tuberculosis); anticoagulants such as heparin (which is not well absorbed by the GI tract and is generally given parenterally, resulting in fluctuation in the blood levels with an increased risk of bleeding at high levels and risks of inefficacy at lower levels) and Warfarin (which is absorbed by the GI tract but cannot be administered immediately after abdominal surgery because of the normal ileus following the procedure); antidepressants (e.g., in situations where compliance is an issue as in Alzheimer's disease or when maintaining stable blood levels results in a significant reduction of anti-cholinergic side effects and better tolerance by patients), such as amitriptylin, imipramin, prozac, etc.; antihypertensive drugs (e.g., to improve compliance and reduce side effects associated with fluctuating blood levels), such as diuretics and beta-blockers (which can be administered by the same patch; e.g., furosemide and propanolol); antipsychotics (e.g., to facilitate compliance and make it easier for care giver and family members to make sure that the drug is received), such as haloperidol and chlorpromazine; and anxiolytics or sedatives (e.g., to avoid the reduction of alertness related to high blood levels after oral administration and allow a continual benefit throughout the day by maintaining therapeutic levels constant).

Numerous other drugs may be administered as described herein, including naturally occurring and synthetic hormones, growth factors, proteins and peptides. For example, insulin and human growth hormone, growth factors like erythropoietin, interleukins and inteferons may be delivered via the skin.

Kits for administering a drug via the skin of a mammal are also provided within the present invention. Such kits generally comprise a device for transdermal application (e.g., a skin patch) in combination with, or impregnated with, one or more modulating agents. A drug may additionally be included within such kits.

Within a related aspect, the use of modulating agents as described herein to increase skin permeability may also facilitate sampling of the blood compartment by passive diffusion, permitting detection and/or measurement of the levels of specific molecules circulating in the blood. For example, application of one or more modulating agents to the skin, via a skin patch as described herein, permits the patch to function like a sponge to accumulate a small quantity of fluid containing a representative sample of the serum. The patch is then removed after a specified amount of time and analyzed by suitable techniques for the compound of interest (e.g., a medication, hormone, growth factor, metabolite or marker). Alternatively, a patch may be impregnated with reagents to permit a color change if a specific substance (e.g., an enzyme) is detected. Substances that can be detected in this manner include, but are not limited to, illegal drugs such as cocaine, HIV enzymes, glucose and PSA. This technology is of particular benefit for home testing kits.

Within a further aspect, methods are provided for enhancing delivery of a drug to a tumor in a mammal, comprising administering a modulating agent in combination with a drug to a tumor-bearing mammal. In one particularly preferred embodiment, a modulating agent is capable of disrupting cell adhesion mediated by multiple adhesion molecules. For example, a single branched modulating agent (or multiple agents linked to a single molecule or support material) may disrupt JAM, occludin, claudin, cadherin (classical and/or nonclassical, such as Dsc, Dsg, OB-cadherin and/or VE-cadherin) and integrin mediated cell adhesion, thereby disrupting tight junctions, adherens junctions, and desmosomes. Multifunctional modulating agents comprising the JAM CAR sequence DPK linked to one or more of the classical cadherin CAR sequence HAV; the sequence RGD, which is bound by integrins; and/or a nonclassical cadherin CAR sequence, such as a Dsc CAR sequence (IEK, VER or IER), a Dsg CAR sequence (INQ, INR or LNK), an occludin CAR sequence (LYHY; SEQ ID NO:6), a claudin CAR sequence (IYSI (SEQ ID NO:7), an OB-cadherin CAR sequence (DDK, EEY or EAQ) and/or the VE-cadherin CAR sequence DAE, may be used to disrupt cell adhesion. Alternatively, a separate modulator of non-JAM- mediated cell adhesion may be administered in conjunction with the modulating agent(s), either within the same pharmaceutical composition or separately. Preferred antibody modulating agents that may be used in conjunction with the JAM modulating agents include Fab fragments directed against either an N-cadherin CAR sequence (such as FHLRAHAVDINGNQV-NH$_2$; SEQ ID NO:9) or an E-cadherin CAR sequence LFSHAVSSNG-NH$_2$ (SEQ ID NO:14), an occludin CAR sequence, such as QYLYHYCVVD-NH$_2$ (SEQ ID NO:12), an OB-cadherin CAR sequence, such as IFVIDDKSG-NH$_2$ (SEQ ID NO:13), a VE-cadherin CAR sequence such as VFRVDAETG-NH$_2$ (SEQ ID NO:10) or a claudin CAR sequence such as WKIYSYAG-NH$_2$ (SEQ ID NO:11).

Preferably, the modulating agent and the drug are formulated within the same composition or drug delivery device prior to administration. In general, a modulating agent may enhance drug delivery to any tumor, and the method of administration may be chosen based on the type of target tumor. For example, injection or topical administration as described above may be preferred for melanomas and other accessible tumors (e.g., metastases from primary ovarian tumors may be treated by flushing the peritoneal cavity with the composition). Other tumors (e.g., bladder tumors) may be treated by injection of the modulating agent and the drug (such as mitomycin C) into the site of the tumor. In other instances, the composition may be administered systemically, and targeted to the tumor using any of a variety of specific targeting agents. Suitable drugs may be identified by those of ordinary skill in the art based upon the type of cancer to be treated (e.g., mitomycin C for bladder cancer). In general, the amount of modulating agent administered varies with the method of administration and the nature of the tumor, within the typical ranges provided above, preferably ranging from about 1 μg/mL to about 2 mg/mL, and more preferably from about 10 μg/mL to 1 mg/mL. Transfer of the drug to the target tumor may be evaluated by appropriate means that will be apparent to those of ordinary skill in the art. Drugs may also be labeled (e.g., using radionuclides) to permit direct observation of transfer to the target tumor using standard imaging techniques.

Within a related aspect, the present invention provides methods for treating cancer and/or inhibiting metastasis in a mammal. Cancer tumors are solid masses of cells, growing out of control, which require nourishment via blood vessels. The formation of new capillaries is a prerequisite for tumor growth and the emergence of metastases. Administration of modulating agents as described herein may disrupt the growth of such blood vessels, thereby providing effective therapy for the cancer and/or inhibiting metastasis. Modulating agents may also be used to treat leukemias. In one particularly preferred embodiment, a modulating agent is capable of disrupting cell adhesion mediated by multiple adhesion molecules. For example, a single branched modulating agent (or multiple agents linked to a single molecule or support material) may disrupt JAM, cadherin and integrin mediated cell adhesion, thereby disrupting tight junctions, adherens junctions, focal contacts and desmosomes. Multifunctional modulating agents comprising a JAM CAR sequence linked to one or more of the classical cadherin CAR sequence HAV; the sequence RGD, which is bound by integrins; and/or a nonclassical cadherin CAR sequence, such as a Dsc CAR sequence (IEK, VER and IER), a Dsg CAR sequence (INQ, INR and/or LNK), an OB-cadherin CAR sequence (DDK, EEY or EAQ), an occludin CAR sequence (LYHY; SEQ ID NO:6), and/or the VE-cadherin CAR sequence DAE, may be used to disrupt cell adhesion. Alternatively, a separate modulator of non-JAM-mediated cell adhesion may be administered in conjunction with the modulating agent(s), either within the same pharmaceutical composition or separately. Preferred antibody modulating agents that may be used in conjunction with the JAM modulating agents include Fab fragments directed against either an N-cadherin CAR sequence, such as FHLRAHAVDINGNQV-NH$_2$ (SEQ ID NO:9), an E-cadherin CAR sequence, such as LFSHAVSSNG-NH$_2$ (SEQ ID NO:14), an occludin CAR sequence, such as QYLYHYCVVD-NH$_2$ (SEQ ID NO:12), an OB-cadherin CAR sequence, such as IFVIDDKSG-NH$_2$ (SEQ ID NO:13) or a claudin CAR sequence such as WKIYSYAG-NH$_2$(SEQ ID NO:11).

A modulating agent may be administered alone (e.g., via the skin) or within a pharmaceutical composition. For melanomas and certain other accessible tumors, injection or topical administration as described above may be preferred. For ovarian cancers, flushing the peritoneal cavity with a composition comprising one or more modulating agents may prevent metastasis of ovarian tumor cells. Other tumors (e.g., bladder tumors, bronchial tumors or tracheal tumors) may be treated by injection of the modulating agent into the cavity. In other instances, the composition may be administered systemically, and targeted to the tumor using any of a variety of specific targeting agents, as described above. In general, the amount of modulating agent administered varies depending upon the method of administration and the nature of the cancer, but may vary within the ranges identified above. The effectiveness of the cancer treatment or inhibition of metastasis may be evaluated using well known clinical observations, such as monitoring the level of serum tumor markers (e.g., CEA or PSA).

Within a further related aspect, a modulating agent may be used to inhibit angiogenesis (i.e., the growth of blood vessels from pre-existing blood vessels) in a mammal. Inhibition of angiogenesis may be beneficial, for example, in patients afflicted with diseases such as cancer or arthritis. In one particularly preferred embodiment, a modulating agent is capable of disrupting cell adhesion mediated by multiple adhesion molecules. For example, a single branched modulating agent (or multiple agents linked to a single molecule or support material) may disrupt JAM, occludin, classical cadherin, and integrin mediated cell adhesion, thereby disrupting tight junctions, adherens junctions, and focal contacts. Multifunctional modulating agents comprising a JAM CAR sequence linked to one or more of the classical cadherin CAR sequence HAV, the sequence RGD, which is bound by integrins, the OB-cadherin CAR sequence (DDK, EEY or EAQ), the occludin CAR sequence (LYHY; SEQ ID NO:6), a claudin CAR sequence IYSY (SEQ ID NO:7) and/or the VE-cadherin CAR sequence DAE may be used to disrupt cell adhesion. Alternatively, a separate modulator of non-JAM-mediated cell adhesion may be administered in conjunction with the modulating agent(s), either within the same pharmaceutical composition or separately. Preferred antibody modulating agents that may be used in conjunction with the JAM modulating agents include Fab fragments directed against an N-cadherin CAR sequence, such as FHLRAHAVDINGNQV-NH$_2$ (SEQ ID NO:9) an occludin CAR sequence, such as QYLYHYCVVD-NH$_2$ (SEQ ID NO:12), an OB-cadherin CAR sequence, such as IFVIDDKSG-NH$_2$ (SEQ ID NO:13), a VE-cadherin CAR sequence such as VFRVDAETG-NH$_2$ (SEQ ID NO:10) or a claudin CAR sequence such as WKIYSYAG-NH$_2$ (SEQ ID NO:11).

The effect of a particular modulating agent on angiogenesis may generally be determined by evaluating the effect of the agent on blood vessel formation. Such a determination may generally be performed, for example, using a chick chorioallantoic membrane assay (Iruela-Arispe et al., *Molecular Biology of the Cell* 6:327–343, 1995). Briefly, a modulating agent may be embedded in a mesh composed of vitrogen at one or more concentrations (e.g., ranging from about 5 to 50 μg/mesh). The mesh(es) may then be applied to chick chorioallantoic membranes. After 24 hours, the effect of the modulating agent may be determined using computer assisted morphometric analysis. A modulating agent should inhibit angiogenesis by at least 25% at a concentration of 50 μg/mesh.

The addition of a targeting agent as described above may be beneficial, particularly when the administration is systemic. Suitable modes of administration and dosages depend upon the condition to be prevented or treated but, in general, administration by injection is appropriate. Dosages may vary as described above. The effectiveness of the inhibition may be evaluated grossly by assessing the inability of the tumors to maintain their growth and microscopically by observing an absence of nerves at the periphery of the tumor.

In yet another related aspect, the present invention provides methods for inducing apoptosis in a JAM-expressing cell. In general, patients afflicted with cancer may benefit from such treatment. In one particularly preferred embodiment, a modulating agent is capable of disrupting cell adhesion mediated by multiple adhesion molecules. For example, a single branched modulating agent (or multiple agents linked to a single molecule or support material) may disrupt JAM, occludin, claudin, classical cadherin, and integrin mediated cell adhesion, thereby disrupting tight junctions, adherens junctions, and focal contacts. Multifunctional modulating agents comprising a JAM CAR sequence linked to one or more of the cadherin CAR sequence HAV and/or the sequence RGD, which is bound by integrins, a claudin CAR sequence IYSY (SEQ ID NO:7), an OB-cadherin CAR sequence DDK and/or an occludin CAR sequence LYHY (SEQ ID NO:6) may be used to disrupt cell adhesion. Alternatively, a separate modulator of non-JAM-mediated cell adhesion may be administered in conjunction with the modulating agent(s), either within the same pharmaceutical composition or separately. Preferred antibody modulating agents that may be used in conjunction with the JAM modulating agents include Fab fragments directed against either an N-cadherin CAR sequence, such as FHLRAHAVDINGNQV-NH$_2$ (SEQ ID NO:9), or an E-cadherin CAR sequence, such as LFSHAVSSNG-NH$_2$ (SEQ ID NO:14), an occludin CAR sequence, such as QYLYHYCVVD-NH$_2$ (SEQ ID NO:12), an OB-cadherin CAR sequence, such as IFVIDDKSG-NH$_2$ (SEQ ID NO:13) or a claudin CAR sequence such as WKIYSYAG-NH$_2$ (SEQ ID NO:11).

Administration of modulating agents to induce apoptosis may be topical, via injection or by other means, and the addition of a targeting agent may be beneficial, particularly when the administration is systemic. Suitable modes of administration and dosages depend upon the location and nature of the cells for which induction of apoptosis is desired but, in general, dosages may vary as described above. A biopsy may be performed to evaluate the level of induction of apoptosis.

The present invention also provides methods for enhancing drug delivery to the central nervous system of a mammal. The blood/brain barrier is largely impermeable to most neuroactive agents, and delivery of drugs to the brain of a mammal often requires invasive procedures. Using a modulating agent as described herein, however, delivery may be by, for example, systemic administration of a modulating agent-drug-targeting agent combination, injection of a modulating agent (alone or in combination with a drug and/or targeting agent) into the carotid artery or application of a skin patch comprising a modulating agent to the head of the patient. In one particularly preferred embodiment, a modulating agent is capable of disrupting cell adhesion mediated by multiple adhesion molecules. For example, a single branched modulating agent (or multiple agents linked to a single molecule or support material) may disrupt JAM, occludin and cadherin mediated cell adhesion, thereby disrupting tight junctions and adherens junctions. Multi-functional modulating agents comprising a JAM CAR sequence linked to one or more of the classical cadherin CAR sequence HAV, the occludin CAR sequence LYHY (SEQ ID NO:6), a claudin CAR sequence IYSY (SEQ ID NO:6), the OB-cadherin CAR sequence (DDK, EEY or EAQ) and/or the VE-cadherin CAR sequence DAE, preferably by way of a linker, are also preferred. Alternatively, a separate modulator of non-JAM-mediated cell adhesion may be administered in conjunction with the modulating agent (s), either within the same pharmaceutical composition or separately. Preferred antibody modulating agents that may be used in conjunction with the JAM modulating agents include Fab fragments directed against the N-cadherin CAR sequence FHLRAHAVDINGNQV-NH$_2$ (SEQ ID NO:9), an occludin CAR sequence, such as QYLYHYCVVD-NH$_2$ (SEQ ID NO:12), an OB-cadherin CAR sequence, such as IFVIDDKSG-NH$_2$ (SEQ ID NO:13), a VE-cadherin CAR sequence such as VFRVDAETG-NH$_2$ (SEQ ID NO:10) or a claudin CAR sequence such as WKIYSYAG-NH$_2$ (SEQ ID NO:11).

In general, the amount of modulating agent administered varies with the method of administration and the nature of the condition to be treated or prevented, but typically varies as described above. Transfer of the drug to the central nervous system may be evaluated by appropriate means that will be apparent to those of ordinary skill in the art, such as magnetic resonance imaging (MRI) or PET scan (positron emitted tomography).

In certain other aspects, the present invention provides methods for enhancing adhesion of JAM-expressing cells. Within certain embodiments, a modulating agent may be linked to a solid support, resulting in a matrix that comprises multiple modulating agents. Within one such embodiment, the support is a polymeric matrix to which modulating agents and molecules comprising other CAR sequence(s) are attached (e.g., modulating agents and molecules comprising HAV and RGD sequences may be attached to the same matrix, preferably in an alternating pattern). Such matrices may be used in contexts in which it is desirable to enhance adhesion mediated by multiple cell adhesion molecules. Alternatively, the modulating agent itself may comprise multiple JAM CAR sequences or antibodies (or fragments thereof), separated by linkers as described above. Either way, the modulating agent(s) function as a "biological glue" to bind multiple JAM-expressing cells within a variety of contexts.

Within one such aspect, modulating agents comprising multiple JAM CAR sequences and/or multiple modulating agents linked to a single molecule or support material may be used to enhance wound healing and/or reduce scar tissue in a mammal. Modulating agents that are linked to a biocompatible and biodegradable matrix such as cellulose or collagen are particularly preferred. For use within such methods, a modulating agent should have a free amino or hydroxyl group. The modulating agents are generally administered topically to the wound, where they may facilitate closure of the wound and may augment, or even replace, stitches. Similarly, administration of matrix-linked modulating agents may facilitate cell adhesion in skin grafting and prosthetic implants, and may prolong the duration and usefulness of collagen injection. In general, the amount of matrix-linked modulating agent administered to a wound, graft or implant site varies with the severity of the wound and/or the nature of the wound, graft, or implant, but may vary as discussed above. Multi-functional modulating agents comprising the JAM CAR sequence DPK, the claudin CAR sequence IYSY (SEQ ID NO:7), the classical cadherin CAR sequence (HAV), the integrin CAR sequence (RGD), the occludin CAR sequence LYHY (SEQ ID NO:6), as well as a nonclassical cadherin CAR sequence, such as the OB-cadherin CAR sequence (DDK, EEY or EAQ), the VE-cadherin CAR sequence DAE and/or one or more of the Dsc and Dsg CAR sequences IEK, VER, IER, INQ, INR and/or LNK, may also be used as potent stimulators of wound healing and/or to reduce scar tissue. Alternatively, one or more separate modulator of cadherin-, integrin-, and/or nonclassical cadherin-mediated cell adhesion may be administered in conjunction with the modulating agent(s), either within the same pharmaceutical composition or separately.

Within another aspect, one or more modulating agents may be linked to the interior surface of a tissue culture plate or other cell culture support, such as for use in a bioreactor. Such linkage may be performed by any suitable technique, as described above. Modulating agents linked in this fashion may generally be used to immobilize JAM-expressing cells. For example, dishes or plates coated with one or more modulating agents may be used to immobilize JAM-expressing cells within a variety of assays and screens. Within bioreactors (i.e., systems for large scale production of cells or organoids), modulating agents may generally be used to improve cell attachment and stabilize cell growth. Modulating agents may also be used within bioreactors to support the formation and function of highly differentiated organoids derived, for example, from dispersed populations of fetal mammalian cells. Bioreactors containing biomatrices of modulating agent(s) may also be used to facilitate the production of specific proteins.

Modulating agents as described herein may be used within a variety of bioreactor configurations. In general, a bioreactor is designed with an interior surface area sufficient to support large numbers of adherent cells. This surface area can be provided using membranes, tubes, microtiter wells, columns, hollow fibers, roller bottles, plates, dishes, beads or a combination thereof. A bioreactor may be compartmentalized. The support material within a bioreactor may be any suitable material known in the art; preferably, the support material does not dissolve or swell in water. Preferred support materials include, but are not limited to, synthetic polymers such as acrylics, vinyls, polyethylene, polypropylene, polytetrafluoroethylene, nylons, polyurethanes, polyamides, polysulfones and poly(ethylene terephthalate); ceramics; glass and silica.

Within further aspects, the present invention provides methods for reducing backleak in kidney transplant patients. This is a problem encountered by kidney transplant patients who are experiencing renal failure, in which the filtrate in the tubules of the kidney leaks back into the kidney. Backleak appears to be the result of impaired integrity of tight junctions (see Kwon et al., *J. Clin Invest.* 101:2054–2064, 1998). Modulating agents that enhance JAM-mediated cell adhesion may be administered to the patient to alleviate backleak. The modulating agents may be administered topically at the time of transplant, or systemically (e.g., intravenously). Multi-functional modulating agents comprising the JAM CAR sequence DPK in combination with CAR sequence(s) of adhesion molecules that are involved in tight junction formation may also be used. Such CAR sequences include the claudin CAR sequence IYSY (SEQ ID NO:7), the classical cadherin CAR sequence (HAV) and the occludin CAR sequence LYHY (SEQ ID NO:6). Alternatively, one or more separate modulator of cadherin-, occludin-, and/or claudin-mediated cell adhesion may be administered in conjunction with the modulating agent(s), either within the same pharmaceutical composition or separately.

Other aspects of the present invention provide methods that employ antibodies raised against the modulating agents for diagnostic and assay purposes. Assays typically involve using an antibody to detect the presence or absence of JAM (free or on the surface of a cell), or proteolytic fragment containing the EC1 domain in a suitable biological sample, such as tumor or normal tissue biopsies, blood, lymph node, serum or urine samples, or other tissue, homogenate, or extract thereof obtained from a patient.

There are a variety of assay formats known to those of ordinary skill in the art for using an antibody to detect a target molecule in a sample. See, e.g., Harlow and Lane, *Antibodies: A Laboratory Manual,* Cold Spring Harbor Laboratory, 1988. For example, the assay may be performed in a Western blot format, wherein a protein preparation from the biological sample is submitted to gel electrophoresis, transferred to a suitable membrane and allowed to react with the antibody. The presence of the antibody on the membrane may then be detected using a suitable detection reagent, as described below.

In another embodiment, the assay involves the use of antibody immobilized on a solid support to bind to the target JAM, or a proteolytic fragment containing the EC1 domain and encompassing the CAR sequence, and remove it from the remainder of the sample. The bound JAM may then be detected using a second antibody or reagent that contains a reporter group. Alternatively, a competitive assay may be utilized, in which the JAM is labeled with a reporter group and allowed to bind to the immobilized antibody after incubation of the antibody with the sample. The extent to which components of the sample inhibit the binding of the labeled JAM to the antibody is indicative of the reactivity of the sample with the immobilized antibody, and as a result, indicative of the level of the JAM in the sample.

The solid support may be any material known to those of ordinary skill in the art to which the antibody may be attached, such as a test well in a microtiter plate, a nitrocellulose filter or another suitable membrane. Alternatively, the support may be a bead or disc, such as glass, fiberglass, latex or a plastic such as polystyrene or polyvinylchloride. The antibody may be immobilized on the solid support using a variety of techniques known to those in the art, which are amply described in the patent and scientific literature.

In certain embodiments, the assay for detection of JAM in a sample is a two-antibody sandwich assay. This assay may be performed by first contacting an antibody that has been immobilized on a solid support, commonly the well of a microtiter plate, with the biological sample, such that the JAM within the sample is allowed to bind to the immobilized antibody (a 30 minute incubation time at room temperature is generally sufficient). Unbound sample is then removed from the immobilized JAM-antibody complexes and a second antibody (containing a reporter group such as an enzyme, dye, radionuclide, luminescent group, fluorescent group or biotin) capable of binding to a different site on the JAM is added. The amount of second antibody that remains bound to the solid support is then determined using a method appropriate for the specific reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products. Standards and standard additions may be used to determine the level of JAM in a sample, using well known techniques.

The present invention also provides kits for use in such immunoassays. Such kits generally comprise one or more antibodies, as described above. In addition, one or more additional compartments or containers of a kit generally enclose elements, such as reagents, buffers and/or wash solutions, to be used in the immunoassay.

Within further aspects, modulating agents or antibodies (or fragments thereof) may be used to facilitate cell identification and sorting in vitro or imaging in vivo, permitting the selection of cells expressing JAM (or different JAM levels). Preferably, the modulating agent(s) or antibodies for use in such methods are linked to a detectable marker. Suitable markers are well known in the art and include radionuclides, luminescent groups, fluorescent groups, enzymes, dyes, constant immunoglobulin domains and biotin. Within one preferred embodiment, a modulating agent linked to a fluorescent marker, such as fluorescein, is contacted with the cells, which are then analyzed by fluorescence activated cell sorting (FACS).

Antibodies or fragments thereof may also be used within screens of combinatorial or other nonpeptide-based libraries to identify other compounds capable of modulating JAM-mediated cell adhesion. Such screens may generally be performed using an ELISA or other method well known to those of ordinary skill in the art that detect compounds with a shape and structure similar to that of the modulating agent. In general, such screens may involve contacting an expression library producing test compounds with an antibody, and detecting the level of antibody bound to the candidate compounds. Compounds for which the antibody has a higher affinity may be further characterized as described herein, to evaluate the ability to modulate JAM-mediated cell adhesion.

The following Example is offered by way of illustration and not by way of limitation.

EXAMPLE 1

Preparation of Representative Cyclic Peptides

This Example illustrates the solid phase synthesis of representative linear and cyclic peptides as modulating agents.

The peptides are assembled on methylbenzhydrylamine resin (MBHA resin) for the C-terminal amide peptides. The traditional Merrifield resins are used for any C-terminal acid peptides. Bags of a polypropylene mesh material are filled with the resin and soaked in dichloromethane. The resin packets are washed three times with 5% diisopropylethylamine in dichloromethane and then washed with dichloromethane. The packets are then sorted and placed into a Nalgene bottle containing a solution of the amino acid of interest in dichloromethane. An equal amount of diisopropylcarbodiimide (DIC) in dichloromethane is added to activate the coupling reaction. The bottle is shaken for one hour to ensure completion of the reaction. The reaction mixture is discarded and the packets washed with DMF. The N-α-Boc is removed by acidolysis using a 55% TFA in dichloromethane for 30 minutes leaving the TFA salt of the a-amino group. The bags are washed and the synthesis completed by repeating the same procedure while substituting for the corresponding amino acid at the coupling step. Acetylation of the N-terminal is performed by reacting the peptide resins with a solution of acetic anhydride in dichloromethane in the presence of diisopropylethylamine. The peptide is then side-chain deprotected and cleaved from the resin at 0° C. with liquid HF in the presence of anisole as a carbocation scavenger.

The crude peptides are purified by reversed-phase high-performance liquid chromatography. Purified linear precursors of the cyclic peptides are solubilized in 75% acetic acid at a concentration of 2–10 mg/mL. A 10% solution of iodine in methanol is added dropwise until a persistent coloration was obtained. A 5% ascorbic acid solution in water is then added to the mixture until discoloration. The disulfide bridge containing compounds are then purified by HPLC and characterized by analytical HPLC and by mass spectral analysis.

From the foregoing, it will be evident that although specific embodiments of the invention have been described herein for the purpose of illustrating the invention, various modifications may be made without deviating from the spirit and scope of the invention. Accordingly, the invention is not limited except as by the appended claims.

What is claimed is:

1. A cell adhesion modulating agent that:
   (a) comprises at least five consecutive amino acid residues of a JAM CAR sequence having the formula:

Ser-Phe-Thr-Ile-Asp-Pro-Lys-Ser-Gly (SEQ ID NO:1);

and
   (b) consists of no more than 50 consecutive amino acid residues linked by peptide bonds.

2. A modulating agent according to claim 1, wherein the agent comprises an N-terminal acetyl group.

3. A modulating agent according to claim 1, linked to a drug.

4. A modulating agent according to claim 1, linked to a detectable marker.

5. A modulating agent according to claim 1, linked to a targeting agent.

6. A modulating agent according to claim 1, linked to a support material.

7. A modulating agent according to claim 6, wherein the support material is a polymeric matrix.

8. A modulating agent according to claim 6, wherein the support material is selected from the group consisting of plastic dishes, plastic tubes, sutures, membranes, ultra thin films, bioreactors and microparticles.

9. A pharmaceutical composition comprising a cell adhesion modulating agent according to claim 1, in combination with a pharmaceutically acceptable carrier.

10. A composition according to claim 9, further comprising a drug.

11. A composition according to claim 9, wherein the cell adhesion modulating agent is present within a sustained-release formulation.

12. A modulating agent according to claim 1, wherein the agent comprises a linear peptide having the sequence SFTIDPKSG (SEQ ID NO:1).

13. A cell adhesion modulating agent that:
   (a) comprises at least seven consecutive amino acid residues of a JAM CAR sequence having the formula:

Ser-Phe-Thr-Ile-Asp-Pro-Lys-Ser-Gly (SEQ ID NO:1);

and
   (b) consists of no more than 50 consecutive amino acid residues linked by peptide bonds.

14. A cell adhesion modulating agent that:
   (a) comprises at least eight consecutive amino acid residues of a JAM CAR sequence having the formula:

Ser-Phe-Thr-Ile-Asp-Pro-Lys-Ser-Gly (SEQ ID NO:1);

and
   (b) consists of no more than 50 consecutive amino acid residues linked by peptide bonds.

\* \* \* \* \*